United States Patent
Ladd et al.

(10) Patent No.: US 8,082,109 B2
(45) Date of Patent: Dec. 20, 2011

(54) COMPUTER-AIDED DISCOVERY OF BIOMARKER PROFILES IN COMPLEX BIOLOGICAL SYSTEMS

(75) Inventors: William M. Ladd, Cambridge, MA (US); Keith O. Elliston, Sudbury, MA (US); Joseph J. Loureiro, Arlington, MA (US)

(73) Assignee: Selventa, Inc., Cambridge, MA (US)

( * ) Notice: Subject to any disclaimer, the term of this patent is extended or adjusted under 35 U.S.C. 154(b) by 555 days.

(21) Appl. No.: 12/200,568

(22) Filed: Aug. 28, 2008

(65) Prior Publication Data
US 2009/0093969 A1 Apr. 9, 2009

Related U.S. Application Data

(60) Provisional application No. 60/968,676, filed on Aug. 29, 2007.

(51) Int. Cl.
*G01N 33/48* (2006.01)
(52) U.S. Cl. ............... 702/19; 435/6; 436/131; 436/501; 514/789
(58) Field of Classification Search ............... 702/19; 435/4, 6, 108, 7.1, 7.9, 7.93, 7.94; 436/144, 436/172, 528, 546, 810, 131, 65, 501, 86, 436/94; 514/789
See application file for complete search history.

(56) References Cited

U.S. PATENT DOCUMENTS

| | | | |
|---|---|---|---|
| 4,385,125 A * | 5/1983 | Preti et al. ............ 436/65 |
| 4,935,877 A | 6/1990 | Koza | |
| 5,136,686 A | 8/1992 | Koza | |
| 5,148,513 A | 9/1992 | Koza et al. | |
| 5,343,554 A | 8/1994 | Koza et al. | |
| 5,390,282 A | 2/1995 | Koza et al. | |
| 5,742,738 A | 4/1998 | Koza et al. | |
| 5,867,397 A | 2/1999 | Koza et al. | |
| 5,914,891 A | 6/1999 | McAdams et al. | |
| 6,058,385 A | 5/2000 | Koza et al. | |
| 6,360,191 B1 | 3/2002 | Koza et al. | |
| 6,424,959 B1 | 7/2002 | Bennett, III et al. | |
| 6,532,453 B1 | 3/2003 | Koza et al. | |
| 6,537,744 B1 * | 3/2003 | Al-Bayati ............ 435/4 |
| 6,564,194 B1 | 5/2003 | Koza et al. | |

(Continued)

FOREIGN PATENT DOCUMENTS

EP 1248231 10/2002

(Continued)

OTHER PUBLICATIONS

International Search Report for PCT/US2007/006877 dated Sep. 25, 2007 (8 pages).

(Continued)

*Primary Examiner* — Carol Tsai
(74) *Attorney, Agent, or Firm* — David H. Judson

(57) ABSTRACT

The invention relates to computational methods, systems and apparatus useful in the analysis of sets of biomolecules in an accessible body fluid or tissue sample from a patient, which biomolecules collectively or individually are candidates to serve as biomarkers, i.e., biomolecules which together or individually upon detection or change are indicative that the patient is in some biological state, such as a diseased state. The methods permit one to examine such potential biological markers to determine whether each one is indeed present as a consequence of the biological state, or as an artifact of the biomarker search protocol.

13 Claims, 17 Drawing Sheets

U.S. PATENT DOCUMENTS

| | | | |
|---|---|---|---|
| 6,594,587 | B2 | 7/2003 | Askenazi |
| 6,665,669 | B2 | 12/2003 | Han et al. |
| 6,741,986 | B2 | 5/2004 | Cho et al. |
| 6,772,160 | B2 | 8/2004 | Cho et al. |
| 2001/0016822 | A1 | 8/2001 | Bessette |
| 2001/0047353 | A1 | 11/2001 | Talib et al. |
| 2002/0002559 | A1 | 1/2002 | Busa |
| 2002/0049782 | A1 | 4/2002 | Herzenberg et al. |
| 2002/0123847 | A1 | 9/2002 | Askenazi |
| 2002/0198858 | A1* | 12/2002 | Stanley et al. .......... 706/50 |
| 2003/0074516 | A1 | 4/2003 | Cho et al. |
| 2004/0249620 | A1 | 12/2004 | Chandra et al. |
| 2005/0165594 | A1* | 7/2005 | Chandra et al. .......... 703/11 |
| 2006/0166242 | A1* | 7/2006 | Pennell et al. .......... 435/6 |
| 2008/0009552 | A1* | 1/2008 | Pennell et al. .......... 514/789 |
| 2009/0298053 | A1* | 12/2009 | Almstrup et al. .......... 435/6 |

FOREIGN PATENT DOCUMENTS

| | | |
|---|---|---|
| WO | WO-02/11048 A2 | 2/2002 |
| WO | WO-02/093409 | 11/2002 |
| WO | WO-03067504 | 8/2003 |
| WO | WO-03/082214 | 10/2003 |
| WO | WO-2005055113 | 6/2005 |

OTHER PUBLICATIONS

Written Opinion of the International Searching Authority for PCT/US2007/006877 dated Sep. 25, 2007 (12 pages).

Pollard, Jr., Ph.D. et al., "A Computational Model to Define the Molecular Causes of Type 2 Diabetes Mellitus," Diabetes Technology and Therapeutics, Vol. 7, No. 2, 2005 (14 pages).

Hartemink et al., "Using Graphical Models and Genomic Expression Data to Statistically Validate Models of Genetic Regulatory Networks," (12 pages).

Pe'er et al., "Minreg: Inferring an active regulator set," Bioinformatics, vol. 18, Suppl. 1 2002 (pp. S258-S267).

International Search Report and Written Opinion of PCT/US2008/074620, completed Nov. 20, 2008 (11 pages).

Center for Development of Advanced Computing, "Workshop on Genetic Algorithms in Bioinformatics,"http://www.cdacindia.com/html/ecents/bioinfo/genetic/genidx.asp, pp. 1-6 (printed Oct. 22, 2002).

Jansen, Ronald, "A Bayesian Networks Approach for Predicting Protein-Protein Interactions from Genomic Data," Science, vol. 302, pp. 449-453 (Oct. 17, 2003).

Karp, Peter D., "The EcoCyc Database," pp. 1-6 (Jan. 25, 2002).

Karp, Peter D., "Integrated Access to Metabolic and Genomic Data," pp. 1-32 (Apr. 1, 1996).

Karp, Peter D., "The MetaCyc Database," pp. 1-7 (Jan. 25, 2002).

Karp, Peter D., "Pathway Databases: A Case Study in Computational Symbolic Theories," Science, vol. 293, pp. 2040-2044 (Sep. 14, 2001).

Karp, Peter D., "The Pathway Tools Software," Bioinformatics, vol. 18 Suppl. 1 2002, pp. S1-S8 (2002).

Koza, John R., "Reverse Engineering and Automatic Synthesis of Metabolic Pathways From Observed Data Using Genetic Programming," pp. 1-53 (2000).

Koza, John R., "Reverse Engineering and Automatic Synthesis of Metabolic Pathways From Observed Data Using Genetic Programming," Symposium on Computational Discovery of Communicatable Knowledge, pp. 1-63 (Mar. 25, 2001).

Koza, John R., "Reverse Engineering and Automatic Synthesis of Metabolic Pathways From Observed Data Using Genetic Programming," Biomedical Informatics, pp. 1-12.

Rindfleisch, Thomas C., "Extracting Molecular Binding Relationships from Biomedical Text," pp. 188-195.

Stevens, Robert "Building a Reason-able Bioinformatics Ontology Using OIL," Department of Computer Science, University of Manchester, p. 1-11.

Yen, John, "A Hybrid Approach to Modeling Metabolic Systems Using Genetic Algorithm and Siomplex Method," pp. 1-42.

Yen, John, "Using Fuzzy Logic and a Hybrid Genetic Algorithm for Metabolic Modeling," pp. 1-6.

International Search Report for PCT/US2003/030653, mailed Feb. 3, 2004.

Goldberg, David E., "Genetic and Evolutionary Algorithms Come of Age," Communications of the ACM, vol. 37, No. 3, Mar. 1994, pp. 113-119.

Van Helden, Jacques, et al., "Representing and Analyzing Molecular and Cellular Function Using the Computer," Biol. Chem., vol. 381, pp. 921-935, Sep.-Oct. 2000.

Uetz P., et al. "Visualization and integration of protein-protein interactions." Retrieved from the Internet: URL:http://itgmv1.fzk.de/www/itg/uetz/publications/Visualization.pdf.

International Search Report for International Application No. PCT/US/2005/00202 mailed from the International Searching Authority on Nov. 24, 2005.

Written Opinion of the International Searching Authority for International Application No. PCT/US/2005/00202 mailed from the International Searching Authority on Nov. 24, 2005.

International Preliminary Report on Patentability for PCT/US2004/039159 dated May 29, 2006.

Written Opinion of the International Searching Authority for PCT/US2004/039159 dated May 29, 2006.

International Search Report for PCT/US03/36857, mailed Mar. 9, 2005.

International Search Report for International Application No. PCT/US/2004/039159 mailed from the International Searching Authority on Aug. 31, 2005.

International Preliminary Report on Patentability for PCT/US2004/039159 dated May 29, 2006.

Written Opinion of the International Searching Authority for PCT/US2004/039159 dated May 29, 2006.

Written Opinion of the International Searching Authority for International Application No. PCT/US/2004/039159 mailed from the International Searching Authority on Aug. 31, 2005.

* cited by examiner

Root node as Observation

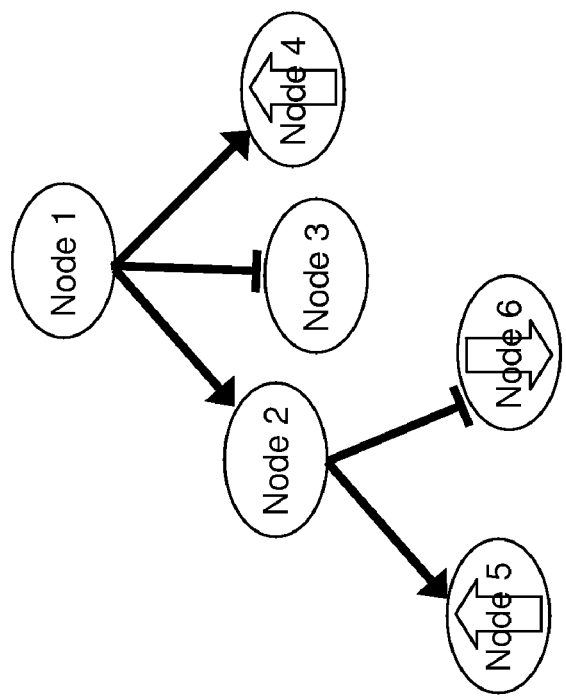
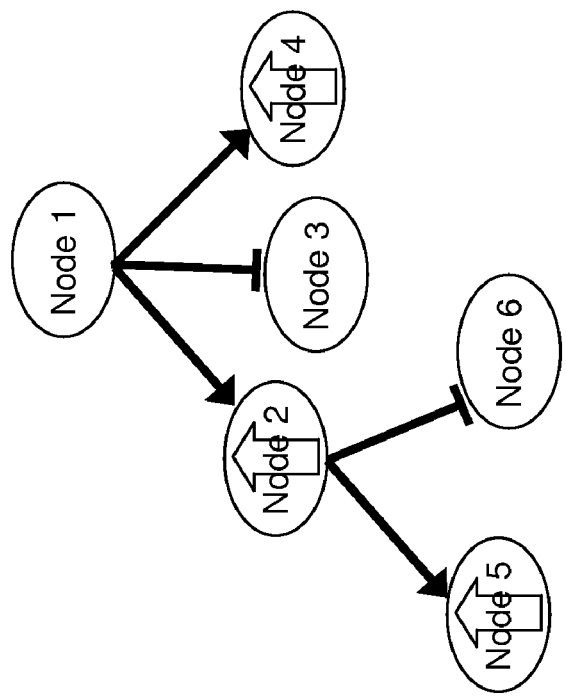
Along a Path
Figure 9

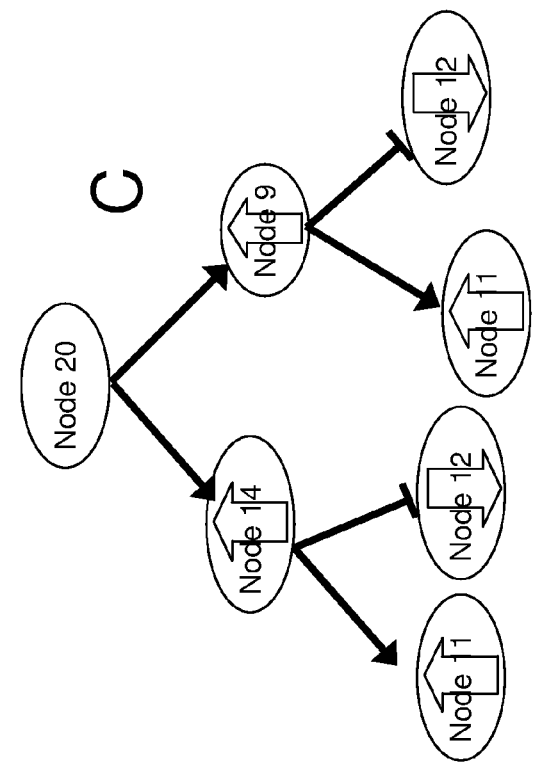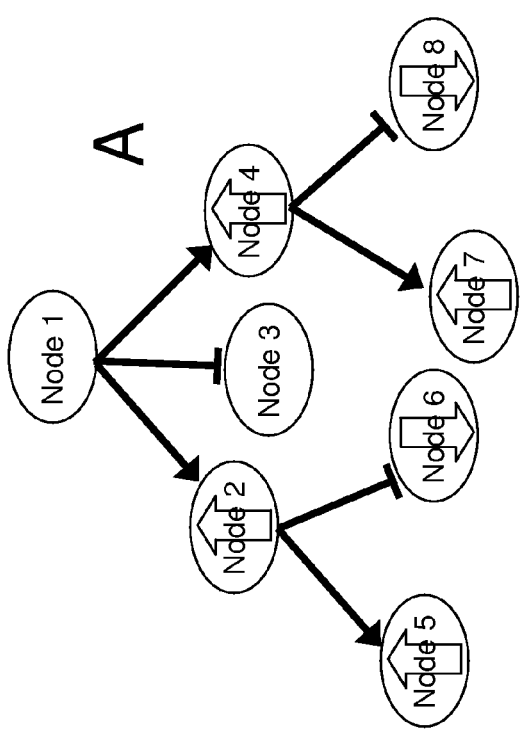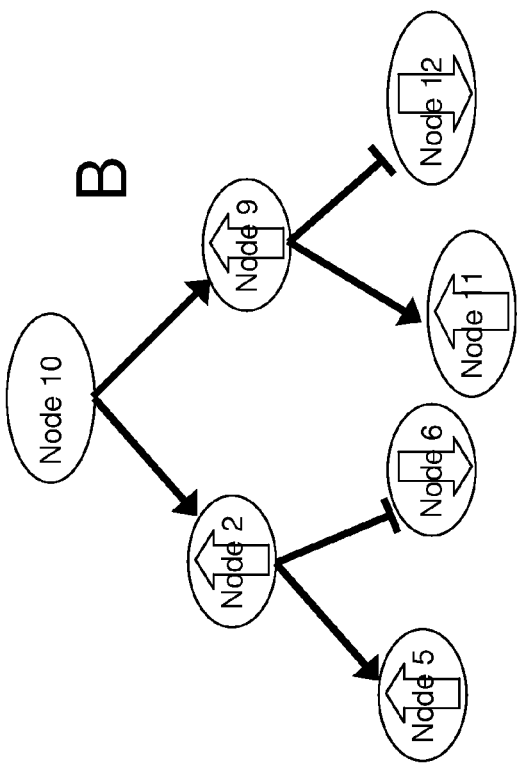
Figure 10

Figure 12
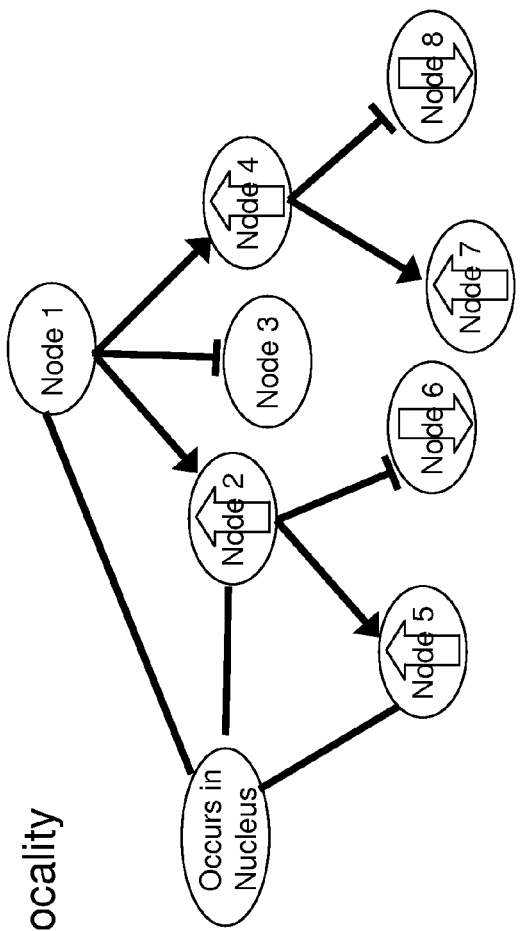
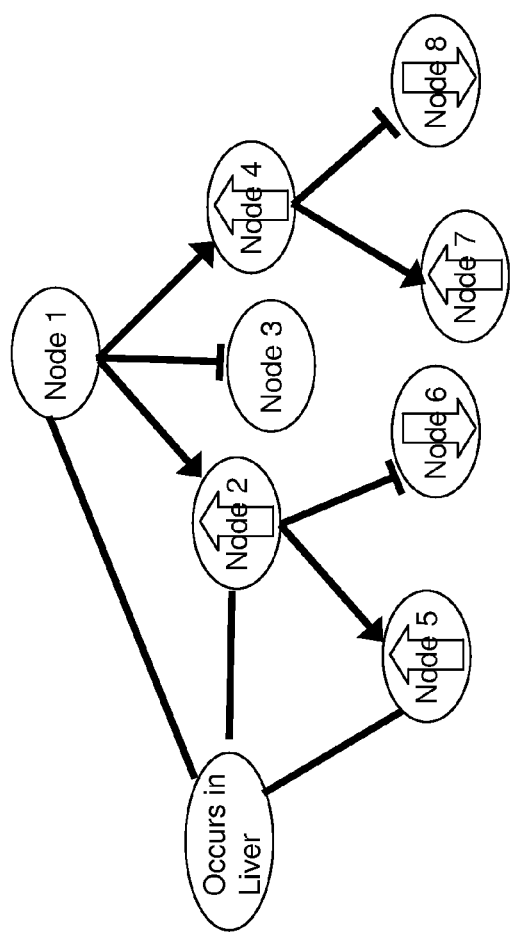

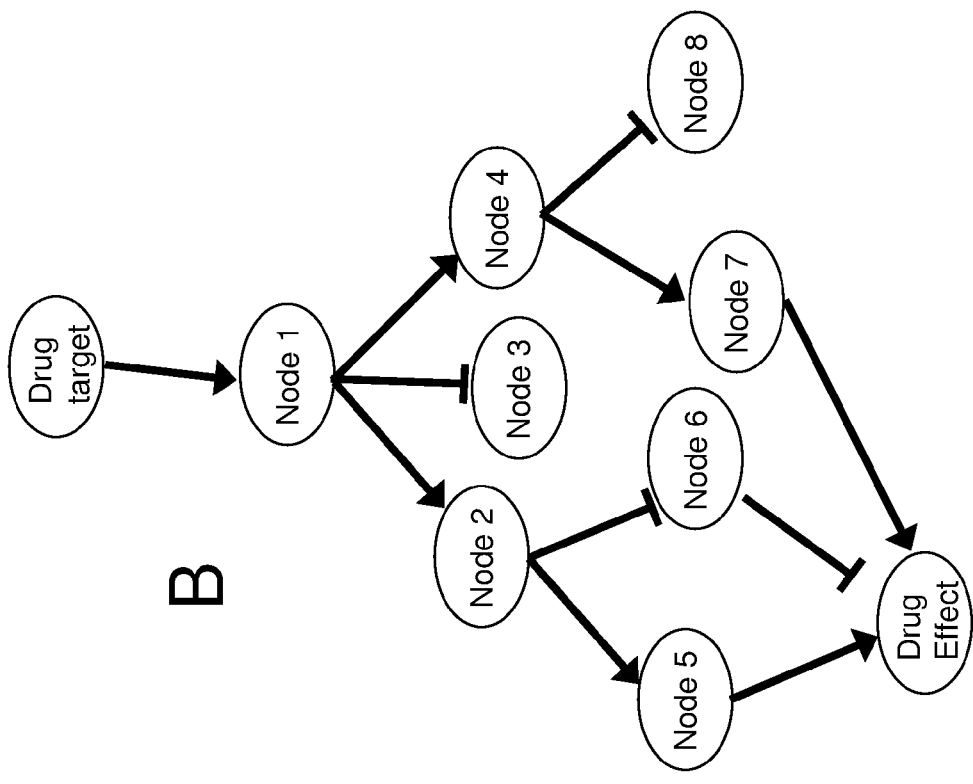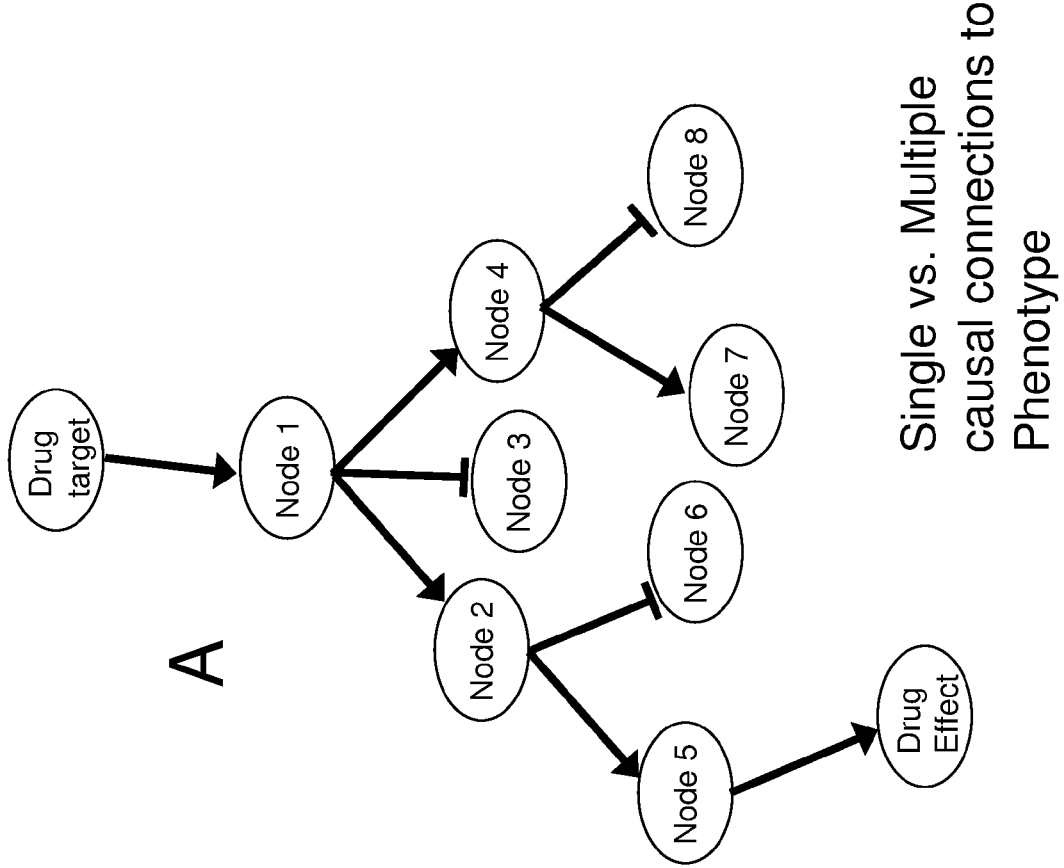
Figure 14

COMPUTER-AIDED DISCOVERY OF BIOMARKER PROFILES IN COMPLEX BIOLOGICAL SYSTEMS

RELATED APPLICATIONS

This application claims the benefit of and priority to U.S. Provisional Patent Application Ser. No. 60/968,676, filed Aug. 29, 2007, the entire disclosure of which is incorporated by reference herein.

TECHNICAL FIELD

The invention relates to computational methods, systems and apparatus useful in the analysis of sets of biomolecules in an accessible body fluid or tissue sample from a patient, which biomolecules collectively or individually are candidates to serve as biomarkers, i.e., biomolecules which together or individually upon detection or change are indicative that the patient is in some biological state, such as a diseased state. The methods permit one to examine such potential biological markers to determine whether each one is indeed present as a consequence of the biological state, or as an artifact of the biomarker search protocol. The methods comprise an extension or improvement on the subject matter claimed in copending U.S. application Ser. No. 11/390,496 filed Mar. 27, 2006 (U.S. patent application Publication Number US2007-0225956A1), the disclosure of which is incorporated by reference. That application, titled Causal Analysis in Complex Biological Systems, discloses methods for analyzing causal implications in complex biological networks, and to computational methods, systems and apparatus for determining which of a multitude of possible hypotheses explanatory of an observed or hypothesized biological effect is most likely to be correct, i.e., most likely to conform with the reality of the biology under study.

BACKGROUND

An important challenge in the understanding of biological systems and in the development of diagnostics, prognostics, and predicted drug responses for complex, multi-factorial diseases is the identification and validation of biomarker profiles or "surrogate markers." It appears that biomarker patterns or sets of biomolecules have more information content than single markers in many contexts. Development of such profiles will permit, among other utilities, a physician to characterize and diagnose homeostasis or disease states in his patients. Typically, molecules from multiple levels of molecular biology, e.g., the polynucleotide (DNA or RNA), polypeptide, and metabolite levels, of the biological system under study, e.g., a human, will be considered simultaneously in the analysis.

The protocols for finding such biomarkers broadly involve analysis of the biomolecular content of a sample such as a body fluid or stool in a number of patients including (1) a test group which has been diagnosed to in fact be in the biological state under study (e.g., suffering from a disease such as cirrhosis of the liver, or having a successful response to an experimental drug); and (2) a control group matched as closely as possible to the test group in terms of sex, race, diet, etc., but known not to be in the biological state under study. The analytical procedure is designed to find, ideally, one, but typically a plurality of biomolecules in the biological samples from patients in the test group that are not present in the control group, or perhaps more typically, that vary reliably in abundance as compared with the control group. This one or set of biomolecules, or some relationship among the concentrations of the biomolecules, is taken as a candidate biomarker or profile of the disease. This in turn is validated by analysis of patients with and without the disease to determine the sensitivity and specificity of the marker.

In practice, many such putative profiles or biomarkers upon validation testing are found to have poor sensitivity or specificity or both, often so poor as to be essentially worthless as a basis for a diagnostic or prognostic test. There are many reasons for this rooted in the complexity of human physiology and biochemistry. The markers may or may not be closely connected to the biology of the disease, and therefore often are unreliable. However, if such empirically determined profiles could be examined for biological state relevance before the costly validation step, the discovery of truly informative biomarker profiles would be facilitated. Furthermore, if a system could be devised that can discern the fundamental difference between biological states of a cell, tissue, organ, organ system, or organism such as diseased and healthy states, then the biomolecular changes discovered to be inherent in the change from a healthy state to a diseased state could be used as clues to what biomolecular changes should occur in the blood (or urine, saliva, stool, csf, tears, etc.). This would provide a theoretical basis for biomarker development, and remove it from the purely empirical realm.

The amount of biological information currently generated per unit time is increasing dramatically. It is estimated that the amount of information now doubles every four to five years. Because of the large amount of information that must be processed and analyzed, traditional methods of analyzing and understanding the meaning of information in the life science-related areas are breaking down. Statistical techniques, while useful, do not provide a biologically motivated explanation of function.

There are ongoing attempts to produce electronic models of biological systems designed to facilitate biological analysis. These involve compilation and organization of enormous amounts of data, and construction of a system that can operate on the data to simulate the behavior of a biological system. Because of the complexity of biology, and the sheer numbers of data, the construction of such a system can take hundreds of man years and multiple tens of millions of dollars. Furthermore, those seeking new insights and new knowledge in the life sciences are presented with the ever more difficult task of selecting the right data from within mountains of information gleaned from vastly different sources. Such knowledge bases if enabled could be used to discern the fundamental difference between, for example, diseased and healthy states of a tissue, organ or organism, a successfully or unsuccessfully drugged organism, or a person who will benefit from a drug and one who will not, and theoretically could be valuable in the task of biomarker discovery.

One useful development in this area is disclosed in co-pending U.S. application Ser. No. 10/644,582 filed Aug. 20, 2003 (U.S. patent application Publication Number US2005-0038608A1) entitled "System, Method and Apparatus for Assembling and Mining Life Science Data," the disclosure of which is incorporated herein by reference. This application discloses and enables exploitation of a new paradigm for the recording, organization, access, and application of life science data. The method and program enable establishment and ongoing development of a systematic, ontologically consistent, flexible, optimally accessible, evolving, organic life science knowledge base which can store biological information of many different types, from many different sources, and represent many types of relationships within the life science information. Furthermore, the knowledge base places life science information into a form that exposes the relationships within the information, facilitates efficient knowledge mining, and makes the information more readily comprehensible and available. This knowledge base is structured as a multiplicity of nodes indicative of life science knowledge using a life science taxonomy. Relationship descriptors are assigned to pairs of nodes that correspond to a relationship between the pair, and may themselves comprise nodes. A very large number of nodes are assembled to form the electronic data base, such that every node is joined to at least one other node. It was envisioned that the knowledge base could eventually incorporate the entirety of human life science knowledge from its finest detail to its global effect, and incorporate an endless diversity of biological relationships in thousands of other organisms. Such a life science knowledge base can be used in a manner similar to a library, permitting researchers, physicians, students, drug discovery companies, and many others to access life science information in a way that enhances the understanding of the information, but is far more powerful as a research resource. Small portions of the knowledgebase may be represented graphically as a web of interrelated nodes, but for any significantly biological system, these are beyond rational comprehension because of their complexity.

A second valuable development came from the realization that querying this knowledge base in its holistic form to determine cause and effect relationships in a particular biological space was sometimes cumbersome, as the knowledgebase included vast amounts of data wholly unrelated to the space under investigation. This led to development of a second invention disclosed and claimed in co-pending U.S. application Ser. No. 10/794,407, filed Mar. 5, 2004 (U.S. patent application Publication Number US2005-0154535A1), entitled "Method, System and Apparatus for Assembling and Using Biological Knowledge," the disclosure of which also is incorporated herein by reference. This application discloses and enables production of sub-knowledge bases and derived knowledge bases (called "assemblies") from a global knowledge base by extracting a potentially relevant subset of life science-related data satisfying criteria specified by a user as a starting point, and reassembling a specially focused knowledge base. These then are refined and augmented, and then may be probed, displayed in various formats, and mined using human observation and analysis and using a variety of tools to facilitate understanding and revelation of hidden or subtle interactions and relationships in the biological system they represent, i.e., to produce new biological knowledge.

Another valuable group of inventions are disclosed and claimed in co-pending U.S. application Ser. No. 10/992,973, filed Nov. 19, 2004 (U.S. patent application Publication Number US2005-0165594A1), the disclosure of which is incorporated herein by reference. This application discloses a group of tools for use with the global knowledge base or with an assembly which facilitate hypothesis generation. The tools and methods perform logical simulations within a biological knowledge base and permit more efficient execution of discovery projects in the life sciences-related fields. Logical simulation resembles reasoning in many respects and includes backward logical simulations upstream of cause and effect relationships, which proceeds from a selected node upstream through a path, typically comprising multiple branches, of relationship descriptor nodes to discern a node or group of nodes representing a biomolecule or activity which is hypothetically responsible for an experimentally observed or hypothesized change in the biological system. In short, this type of computation answers the question "What could have caused the observed change?" Logical simulation also includes forward simulations, downstream of cause and effect relationships, which travel from a target node downstream through a path of relationship descriptors to discern the extent to which a perturbation of the target node causes experimentally observed or hypothetical changes in the biological system. The logical simulation travels through a path of relationship descriptors containing at least one potentially causative node or at least one potential effector node to discern a pathway hypothetically linking the target nodes. This in turn permits the generation of new hypotheses concerning biological pathways based on the biological knowledge, and permits the user to design and conduct biological experiments involving biomolecules, cells, animal models, or a clinical trial to validate or refute a hypothesis. The set of these paths comprise explanations for perturbations of the target nodes which hypothetically could be caused by perturbations of the source nodes. The perturbation is induced, for example, by a disease, toxicity, drug reaction, environmental exposure, abnormality, morbidity, aging, or another stimulus.

When an investigation is based on a hypothesized relationship or on an experimentally observed relationship between distinct biological elements, and the goal is to understand the underlying biochemistry and molecular biology causative of the relationship, it often will be the case that numerous potentially explanatory paths will emerge from an in silico analysis. Thus, the foregoing and potentially other related software based biological system analysis techniques can result in a large number of hypotheses including hypotheses that are mutually exclusive, and many which may in fact not be representative of real biology. This is not surprising in view of the extreme complexity of biological systems.

A method utilizing the foregoing technology in a novel way to conduct causal analysis in complex biological systems is disclosed and claimed in copending U.S. application Ser. No. 11/390,496 filed Mar. 27, 2006 U.S. patent application Publication Number US2007-0225956A1), titled "Causal Analysis in Complex Biological Systems," the disclosure of which is incorporated by reference. That application provides software implemented methods of discovering active causative relationships in the biology, e.g., molecular biology, of complex living systems. The method is practiced within the domain of systems biology and is designed to discover the web of interactions of specific biological elements and activities causative of a given biological response or state. It may be practiced using a suitably programmed general purpose computer having access to a biological data base of the type disclosed herein.

The problem solved by this method may be analogized to the task of finding the right pathways within a vast, multi dimensional array or web of selectively interconnected points respectively representing something about a biological molecule or structure, its various activities, its structural variants, and its various relationships with other points to which it connects. A connection indicates that there is a relationship between the two points and optionally the directionality of the relationship, e.g., the node "kinase activity of protein P" might be linked to "quantity of phosphorylated form of protein S", protein P's substrate, by indicia of directionality, indicating node "kaProtP" influences "PhosProtS", and not vice versa. Suppose also that from an observation, it is known that when drug A is administered, it inhibits protein T, and induces a given biological state or states in the organism, e.g., reduced secretion of stomach acid, and in some subjects, induces the onset of inflammatory bowel disease. The question: "what is the mechanism of the effects?" involves finding the pathways within this vast network of connected points that best explain the data, and are most likely to represent real biology. There may be thousands or millions of potential such pathways in a knowledge base, and a large number even in a well targeted assembly.

Generally, the method of the '496 application comprises mapping operational data onto a knowledge base, preferably an assembly, of the type described therein to produce a large number of models—chains defining branching paths of causality propagated virtually through the knowledge base—and applying a series of algorithms to reject, based on various criteria, all or portions of the models judged not to be representative of real biology. This pruning or winnowing process ultimately can result in one or a small number of models which underlie an explanation of the operational data, i.e., reveals causative relationships that can be verified or refuted by experiment and can lead to new biological knowledge.

The method comprises the steps of first providing a knowledge base of biological assertions concerning a selected biological system. The knowledge base comprises a multiplicity of nodes representative of a network of biological entities, actions, functional activities, and biological concepts, and links between nodes indicative of there being a relationship therebetween, at least some of which include indicia of causal directionality. The knowledge base of the above mentioned '582 application; or preferably an assembly of the type disclosed in the above mentioned '407 application targeted to the selected biological system, are examples of such knowledge bases.

The purpose of the system is to aid in the understanding of the biochemical mechanisms explanatory of a data set, herein referred to as "operational data." Operational data is data representative of a perturbation of a biological system, or characteristic of a biological system in a particular biological state, and comprises observed changes (observational data) in levels or states of biological components represented by one or more nodes, and optionally hypothesized changes (hypothetical data) in other nodes resulting from the perturbation(s). The operational data can comprise an effective increase or decrease in concentration or number of a biological element, stimulation or inhibition of activity of an element, alterations in the structure of an element, the appearance or disappearance of an element or phenotype, or the presence or absence of a SNP or allelic variant of a protein. Typically, the operational data is experimentally determined data, i.e., is generated from "wet biology" experiments. Preferably, all of the biological elements recorded as increasing or decreasing, etc., in the operational data are represented in the knowledge base or assembly.

Thus plural models or chains, i.e., paths along connections or links and through nodes within the data base, are identified by software. This typically is done by simulating in the network one or more perturbations of multiple individual root nodes (or starting point nodes) to initiate a cascade of activity through the relationship links along connected nodes preferably to an intermediate or most preferably a terminal node that is representative of a biological element or activity in the operational data. This process produces plural (often $10^4$, $10^5$ or more) branching paths within the knowledge base potentially individually representing at least some portion of the biochemistry of the selected biological system.

These branching paths constituting models are prioritized by applying algorithms to the models which estimate how well each model predicts the operational data. This is done by mapping the operational data onto each candidate model and counting the number of nodes in the model that are representative of, and/or correspond to, elements represented in the operational data.

This results in definition of a smaller set of branching paths comprising hypotheses potentially explanatory of the molecular biology implied by the data. Typically, after such a screening via the mapping algorithm(s), there still are many such branching paths, often hundreds or thousands, depending on the granularity of the assembly or of the knowledge base, on the question in focus, on the prioritization criteria, and on other factors.

The foregoing steps of generating, mapping and prioritizing pathways can be conducted in any order. For example, the software may first map the operational data onto the assembly, then search for branching paths and keep a ranking based on the amount of data correctly simulated, or it may be designed to first identify all possible paths involving a given data point, then map remaining data onto each path and prioritize as mapping proceeds, etc. Preferably, for efficiency, some or all of the operational data is mapped onto the knowledge base or assembly before raw path finding commences, and the paths discerned are constrained to paths which intersect a node corresponding to or at least involved with the data.

At this point, the system has identified a large number of hypotheses, represented as branching paths or models, each of which potentially explain at least some portion of the operational data. The next step in the method is to apply logic based criteria to each member of the set of models to reject paths or portions thereof as not likely representative of real biology. This "hypothesis pruning" leaves one or a small number of remaining models constituting one or more new active causative relationships.

As nonlimiting examples, the logic based criteria may be based on:

A measure of consistency between the predictions resulting from simulation along a model and known biology (e.g., not involving the Using as a filter a group of models generated by mapping against random or control data to eliminate models from the set of models.

An assessment of descriptor nodes associated with each model for consistency with known aspects of the biology of the selected biological system. For example, the assessment may be based on mutual anatomic accessibility of the nodes representing entities in a given branching path, and answers the question: are all biological elements in the path known to be accessible in vivo to its connected neighbors?

A measure of consistency between the operational data and the predictions resulting from simulation along a branching path, and may seek to answer questions such as: does the perturbation of the root node correspond to the operational data, e.g., the observed wet biology data under examination? Does this path which contains, e.g., 7 nodes corresponding to operational data points, predict their increase or decrease consistently with the operational data? What is the number of nodes perturbed in a linear path comprising a portion of a branching path which correspond to the operational data?

A determination of a pair, triad or higher number of branching paths which together best correlate with the operational data. Optimal combinations may be determined by applying combinatorial space search algorithms, such as a genetic algorithm, simulated annealing, evolutionary algorithms, and the like, to the multiple branching paths using as a fitness function the number of correctly simulated data points in the candidate path combinations.

Whether a branching path comprises linear paths wherein plural nodes are perturbed in the same direction as the operational data, or comprising multiple connections to concept nodes, e.g. to nodes representing complex biological conditions or processes under study such as apoptosis, metastasis, hypoglycemia, inflammation, etc.

The method may comprise the additional step of harmonizing a plurality of remaining paths to produce a larger path, to select a subgroup of paths, or to select an individual path comprising a model of a portion of the operation of a the biological system. "Harmonizing" means that plural branching paths are combined to provide a more complete or more accurate model explanatory of the operational data, or that all branching paths except one are eliminated from further consideration.

The method may further comprise the step of simulating operation of the model to make predictions about the selected biological system, for example, to select biomarkers characteristic of a biological state of the selected biological system, or to define one or more biological entities for drug modulation of the system.

The method can be practiced by applying a plurality of logic based criteria to the set of branching paths to approach one or more hypotheses representative of real biology. This approach may employ a scoring system based on multiple criteria indicative of how close a given hypothesis/branching path approaches explanation of the operational data. Collectively, the various features of the hypothesis pruning protocols enable identification of one or more hypotheses which approach known aspects of the biology of the selected biological system and the biological change under study.

SUMMARY OF THE INVENTION

This invention provides a software assisted method of discovering biomarkers in a body fluid or tissue sample from an animal, typically a mammal, such as a human or experimental animal, indicative of a biological state of one or a set of organs or tissues of the animal, or in the animal itself. Broadly, in a first aspect, the method comprises providing one or more models typically in the form of digital data in a data storage medium representative of one or more causative or characteristic biophysical or biochemical relationships underlying the biological state in the cell, tissue, organ, organ system, or organism. The models typically are held in the memory of a computer, and comprise a collection of nodes representing biological entities, actions, functional activities, or concepts, and links between nodes indicative of being a relationship therebetween. At least some of the links determine a causal directionality. Additionally, one provides a candidate profile or biomarker set, typically in the form of digital data representing biomolecules, or concentration relationships between biomolecules, which are hypothesized to be indicative of the biological state of the cell, tissue, organ, organ system or organism. These profile candidates are determined by analysis of a body fluid or tissue sampled from an animal (typically multiple mammals) known to be in the biological state. The body fluid may be, for example, lymph, urine, blood, serum, plasma, saliva, tears, sweat, amniotic fluid, cerebrospinal fluid, stool, tissue lysate preparations, cell lysate preparations, or various pre-processed or digested fractions thereof. Many methods for discovering multiple biomolecules which can act as surrogate markers indicative of a particular biological state such as a diseased state are known in the art.

With these two data sets in hand, one "maps" (i.e. compares) the candidate profile data onto a model to discern which of the features of the profile (biomolecule identity, concentration change relative to control, or relationship of concentration among biomolecules) are indicative of the biological state of the cell, tissue, organ, organism, or organ system, or alternatively, which are unrelated to the biological state, and are just an artifact peculiar to the method used to discern the profile. This permits the researcher to develop informative biomarker profiles found in an accessible body fluid which are reproducibly indicative of the biological state of the relatively inaccessible cell, organ or tissue. The researcher can physically store an electronic representation of the informative biomarker profiles (i.e., candidate biomarkers) on a computer-readable medium for retrieval and use by the researcher or another party (e.g., an investigator). Thus, in this aspect, the model is used as a filter to determine which biomolecules found, e.g., in blood or urine, are present as a consequence of the biological state of the organ, and which ones for unrelated reasons appeared to cluster in the body fluid of the test group, and not the control group.

In another aspect, the invention provides a software assisted method of discovering such biomarkers involving development and study of models informative of the biochemistry in a cell, tissue, organ, organ system, or organism, e.g., a mammal or other organism, so as to enable development of candidate biomarkers on theoretical grounds, i.e., enable development of hypotheses concerning which biomolecules should appear, disappear, be modified (e.g., phosphorylated or de-phosphorylated) increase, or decrease in a body fluid or tissue sample as a consequence of the biological state. This aspect of the method comprises first providing one or more models representative of one or more causative or characteristic relationships underlying the biological state in the organ or tissue. Again, this model may comprise a set of nodes representing a biological entity, action, functional activity, or concept, as well as links between nodes indicative of there being a relationship therebetween, at least some of which determine a causal directionality. These are examined to discern a set of biomolecules or concentration relationships hypothetically to be found in a body fluid and to be indicative of the biological state if present in the cell, tissue, etc. This hypothesis is used as a map to direct the search in body fluid from individuals known to be in the biological state. The biomolecules or concentration relationships that are confirmed to be in the body fluid of individuals having the biological state can serve as candidate biomarkers for the biological state. An electronic representation of a candidate biomarker can be physically stored on a computer-readable medium for retrieval and use by a researcher or another party (e.g., an investigator).

In both aspects of the invention, and in species of the invention which are hybrids of the two extremes disclosed above, the currently preferred methods for generating the provided models are the methods disclosed in copending application Ser. No. 11/390,496 (U.S. patent application Publication Number US2007-0225956A1), discussed above and in more detail hereinafter. In summary, this method involves providing a knowledgebase of biological assertions concerning a selected biological state, the knowledgebase comprising a multiplicity of nodes representative of a network of biological entities, actions, functional activities, and concepts, and links between nodes indicative of there being a relationship between the nodes, wherein at least some of the links determine a causal directionality; simulating in the network one or more perturbations of plural individual root nodes to initiate a cascade of virtual activity through the links between connected nodes to discern multiple branching paths within the knowledgebase; mapping onto the knowledgebase operational data (e.g., data from wet biology experiments) representative of a perturbation, associated with the biological state, of one or more nodes and optionally of experimentally observed or hypothesized changes in other nodes resulting from the one or more perturbations; and prioritizing the branching paths on the basis of how well they predict the operational data. This results in discovery of a set of models comprising branching paths potentially explanatory of the molecular biology implied by the data. Next, one applies logic-based criteria to the set of models to reject models as not likely representative of real biology. This eliminates hypotheses and serves to identify from remaining models one or more active causative relationships. These, in turn, can be refuted or confirmed by wet biology experiments or additional research. Broadly, the operational data may comprise an effective increase or decrease in concentration or number of a biological element, stimulation or inhibition of activity of an element, alterations in the structure of an element, or the appearance or disappearance of an element.

In both aspects of the invention, it is often the case that the biomolecules found using the model that are predicted to be accessible in a body fluid are not (or not all) a part of the causal system model. In other words, it is often the case that the scientist must look one or two steps downstream from a biomolecule present in the model to find the presence, absence, or increase or decrease in abundance that the model predicts should be in, e.g., blood. Thus, the knowledge base can not only be used to form a biochemical model of the disease, but also to predict its consequences, and more specifically, to predict what downstream biomolecules should appear in a body fluid, and whether their concentrations should increase or decrease.

The body fluid preferably is accessible via transdermal needle extraction or by natural secretion (e.g., urination). The biological state may be, for example, a disease state, a homeostatic state, a successfully drugged state, an unsuccessfully drugged state, a toxic state, an environmental state, etc. Exemplary states include cancer of or a metabolic disease involving an organ or tissue. The invention also includes the additional step of obtaining a sample of body fluid from a patient presenting herself for a health checkup or diagnosis, and assaying the sample for the presence of the biomarkers to discern the current biological state of the patient.

Biomolecules which can constitute components of the profile include proteins, (including allelic variants) RNAs, DNAs and particular single nucleotide polymorphisms, metabolites, lipids, sugars, xenobiotics, and various modified forms of such species.

Other aspects of the invention will be apparent from the description and claims that follow. It should be understood that different embodiments of the invention, including those described under different aspects of the invention, are meant to be generally applicable to all aspects of the invention. Any embodiment may be combined with any other embodiment unless inappropriate. All examples are illustrative and non-limiting.

BRIEF DESCRIPTION OF THE DRAWINGS

FIGS. 6-14 are illustrations of models useful in explaining the various computationally based methods of pruning candidate hypotheses;

DETAILED DESCRIPTION

The present invention relates to software assisted systems and methods for aiding in the discovery and development of biomarkers characteristic of a biological state in an organism, such as an animal, or a tissue or organ thereof. The biomarkers comprise one or a collection of biomolecules found in a biosample (e.g., serum, taken from a test population of individuals in the biological state under study) but not in controls, or that are at one or more different levels of abundance in the biosample than in controls. Active causative relationships in the biology of complex living systems are discovered by providing a data base of biological assertions comprising a multiplicity of nodes representative of a network of biological entities, actions, functional activities, and concepts, and relationship links between the nodes. Simulating perturbation of individual root nodes in the network initiates a cascade of virtual activity through the relationship links to discern plural branching paths within the data base comprising a model of the underlying biochemistry of the biological state. Operational data, e.g., experimental data, representative of a real or hypothetical perturbations of one or more nodes are mapped onto the data base. The branching paths or models then are prioritized as hypotheses on the basis of how well they predict the operational data. Logic based criteria are applied to the models to reject models as not likely representative of real biology. The result is a set of remaining models comprising nodes representative of biomolecules within branching paths potentially explanatory of the molecular biology implied by the data.

The presence or absence, or increase or decrease in abundance, of one or more biomolecules in the models then are compared to data derived from one or samples from an individual (e.g., an animal) in the biological state. The comparison allows a researcher to discern the candidate biomolecules in the model (i.e., discern which biomolecules reflect the underlying biology of the biological state and which are artifacts of limited information content).

1. Model Preparation

Figure 1:
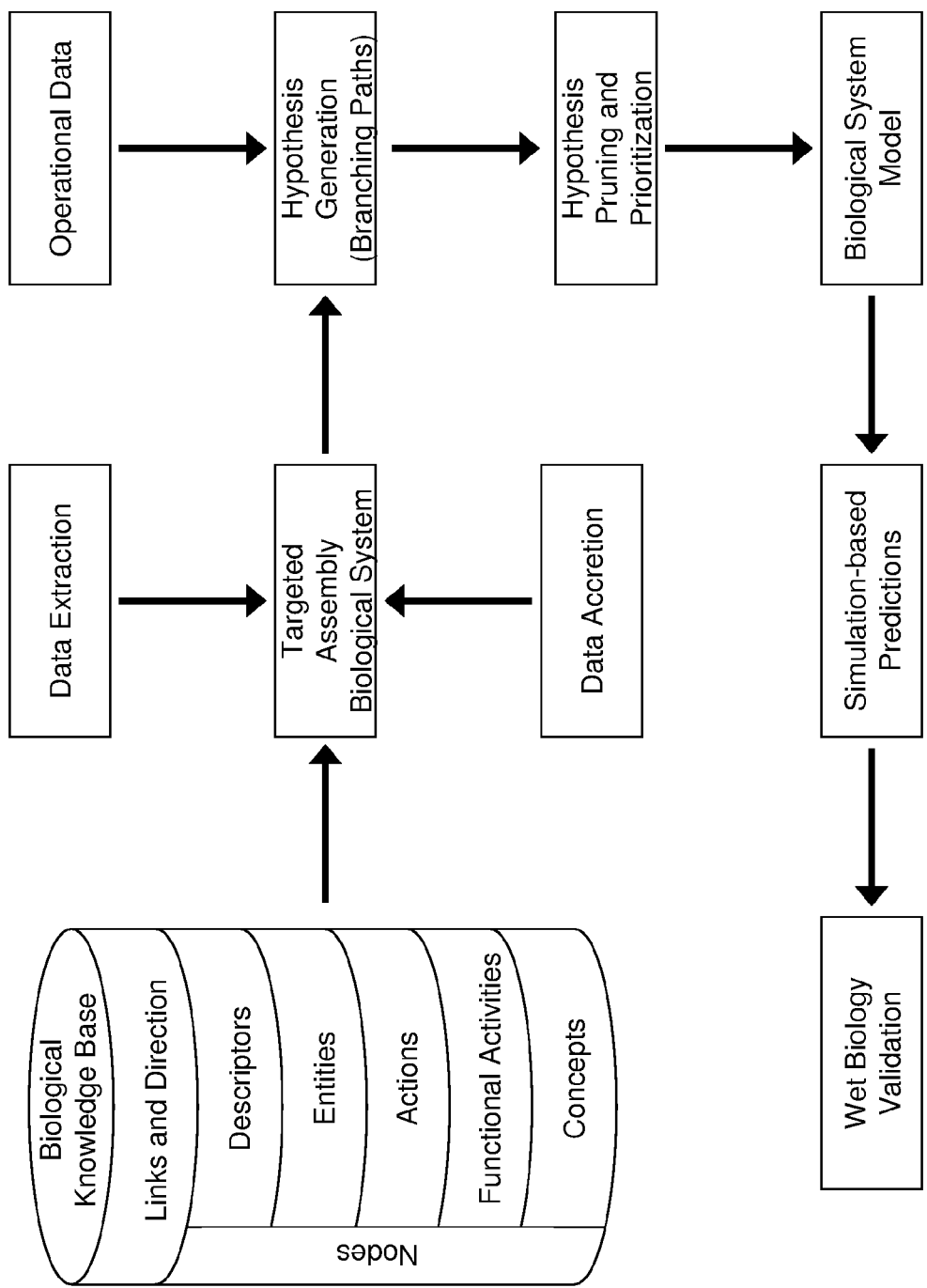
FIG. 1 is a flow chart illustrating the structure of a data base useful in the practice of the invention.

Referring to FIG. 1, the overall logic flow of the methods of the invention is shown. A large reusable biological knowledge base comprises an addressable storehouse of biological information, typically stored in a memory, in the form of a multiplicity of data entries or "nodes" which represent 1) biological entities (biomolecules, e.g., polynucleotides, peptides, proteins, small molecules, metabolites, lipids, etc., and structures, e.g., organelles, membranes, tissues, organs, organ systems, individuals, species, or populations), 2) functional activities (e.g., binding, adherence, covalent modification, multi-molecular interactions (complexes), cleavage of a covalent bond, conversion, transport, change in state, catalysis, activation, stimulation, agonism, antagonism, repression, inhibition, expression, post-transcriptional modification, internalization, degradation, control, regulation, chemo-attraction, phosphorylation, acetylation, dephosphorylation, deacetylation, transportation, transformation, etc.), 3) biological concepts (e.g., metastasis, hyperglycemia, apoptosis, angiogenesis, inflammation, hypertension, meiosis, T-cell activation, etc.), 4) biological actions (inhibit or promote), an 5) biological descriptors (e.g., species or source designations, literature references, underlying structural information, e.g., amino acid sequence, physico-chemical descriptors, anatomical location descriptors, etc.). Any two nodes having a known and curated physical, chemical, or biological relationship are linked. Also designated in the knowledgebase is a direction of causality between a pair of nodes (if known). Thus, for example, a link between catalysis and substrate would be in the direction of the substrate; and a link between a substrate and a product in the direction of product.

Such a comprehensive knowledge base may be difficult to navigate, as it comprises thousands or millions of nodes irrelevant to any specific analysis task. It is therefore preferred to build a sub knowledge base, i.e., to develop a specialty knowledge base specifically adapted for the task at hand. This fundamentally involves extracting from the global knowledge repository, e.g., using Boolean search strategies, all nodes meeting certain user specified criteria, and configuring the extracted nodes to form a sub knowledge base. This can be augmented by, for example, adding to the sub knowledge base new nodes from the literature thought to be potentially pertinent to the topic at hand, altering the granularity of the sub knowledge base in areas of limited interest, and applying logic algorithms to fill in gaps in the paths based on analogous reasoning, extrapolating to the species under study biological paths studied in detail in a different species, etc. This forms a working knowledge base herein referred to as an "assembly."

In the next step of the process, operational data (observed biological data from experiments or hypothetical biological data) is mapped onto the assembly, and algorithms simulate the effect through the assembly of hypothesized increases or decreases in the quantity or activity of nodes within the assembly. This results in generation of a large number of branching paths which involve nodes representative of data points in the operational data set. Some or all of these branching paths or "models" predict an increase or decrease in one or more nodes which are representative of, and preferably corresponds to, an activity or entity in the operational data set. Paths are selected and prioritized on the basis of how many operational data points are involved with the path; generally, the more operational data involved in a path, the more likely it is to be selected for further processing.

In a preferred practice of the method of the invention, the models are evaluated for "richness" and "concordance." Richness refers to resolution of the question whether, with respect to each model, the number of nodes in the model which map onto the data is greater than the number that would map by chance. This is done as set forth hereafter and as explained with reference to FIGS. 6 and 7, and results in identification of a set of branching paths, or hypotheses, potentially explanatory of the operational data. In a given exercise, depending on the biological space under study, the data package involved, the focus of the assembly, and the stringency of the criteria, there may be thousands or hundreds of thousands of such hypotheses. The various branching paths may overlap, involve differing amounts of operational data and may contradict portions of the operational data. This set of paths is then used as the starting material for a process which ultimately may result in discovery of one or more plausible, empirically testable, data driven cause and effect insights, at the level of the biochemistry under investigation.

The process involves winnowing or "hypothesis pruning," and is done by applying logic based, software-implemented criteria to the set of branching paths to reject paths as not likely representative of real biology. This serves to eliminate hypotheses and to identify from remaining hypotheses one or more new active causative relationships. The logic based criteria may be embodied as one or more algorithms, typically many used together, designed fundamentally to eliminate paths not likely to represent real biology. A number of such criteria are disclosed herein as non-limiting examples. Those skilled in the art can devise others.

After this pruning process, one, a few, or perhaps a dozen or so alternative or complementary hypothetical biochemical explanations of the data remain. These may be inspected by a scientist, rejected on the basis of her judgment and other factors not embodied in the software based winnowing algorithms, or accepted at least tentatively, and combined to produce a detailed model of the operational data under study. This "causal system model" in turn may be used to make simulation-based predictions, and these in turn can be validated or refuted by wet biology experimentation.

Preferred ways to make and use the various components of the causal system model of the invention will now be explained in more detail.

1A. The Knowledge Base

As disclosed in detail in U.S. application Ser. No. 10/644, 582 (Publication Number 2005-0038608) filed Aug. 20, 2003 entitled "System, Method and Apparatus for Assembling and Mining Life Science Data," biological and other life sciences knowledge can be represented in a computer environment in a form which permits it to be computationally probed, manipulated, and reasoned upon. Such data structures can be reasoned upon by algorithms that are designed to derive new knowledge and make novel conclusions relevant to furthering the understanding of biological systems and its underlying mechanisms. Providing such a knowledge base permits harmonization of numerous types of life science information from numerous sources.

The knowledge base preferably is constructed using "frames" that represent standard "cases," which permit biological entities and processes to be related in a well-defined patterns. An intuitive "case" is a chemical reaction, where the reaction defines a pattern of relations which connect reactants, products, and catalysts. The case frames provide a representational formalism for life sciences knowledge and data. Most case frames used in the system are derived from "fundamental" terms by functional specification and construction. This technique, essentially similar to skolem terms in formal logic, has been used in previous representation systems, such as the Cyc system (Guha, R. V., D. B. Lenat, K. Pittman, D. Pratt, and M. Shepherd. "Cyc: A Midterm Report." Communications of the ACM 33, no. 8 (August 1990).

Fundamental terms are either created as part of basic biological ontology or derived from public ontologies or taxonomies, such as Entrez Gene, the NCBI species taxonomy, or the Gene Ontology (Gene Ontology: tool for the unification of biology. The Gene Ontology Consortium (2000) Nature Genet. 25: 25-29.). These terms typically are assigned unique identifiers in the system and their relationship to the public sources preferably is carefully maintained. An example of a fundamental term is the protein class "TP53 Homo sapiens," —the class of all proteins which meet the criteria of the TP53 Homo sapiens entry in the Entrez Gene database. Another example is the term "apoptosis," the class of all apoptosis processes meeting the criteria of the Gene Ontology term. Generally, the entries in the system are referred to as "nodes," and these can represent not only biological entities and functional biological activities, but also biological actions (generally one of "inhibit" or "promote") and biological concepts (biological processes or states which themselves are characterized by underlying biochemical complexity).

Some examples of nodes:
kinaseActivityOf(X)
   input: the protein class or a complex class X, where X must be annotated with protein kinase activity
   output: the class of all processes where X acts as a kinase
complexOf(X,Y)
   input: two protein classes or complex classes X and Y
   output: the class of all complexes having exactly X and Y as components
X^Y
   input: two classes of biological entities or processes
   output: the class of all processes in which some members of class X increase the amount, abundance, occurrence, or frequency of members of class Y The functional specification, construction, and retrieval of a case frames system allows the practical use of a very large number of highly specific case frames derived from the ontology of fundamental terms, such as specialized sets of proteins, activities of proteins, processes of increase and decrease, etc. Because a scientist adding knowledge to the knowledgebase can simply refer to new case frames by their specification, the speed and accuracy of data accretion and knowledge modeling is accelerated. For example, to state "MAPK8 proteins, acting as kinases, can increase the transcriptional activity of JUN proteins" reduces to a simple functional expression that returns a case frame representing this process of increase:

kaof(MAPK8)^taof(JUN)

Most important, the use of these specialized case frames allows the modeling of complex biology with many case frames but a small number of relationship types. It enables the relationships in the system to have simple semantics despite the complexity of the biology. A subset of relationships in the system may be designated as "causal" so that causal reasoning algorithms can use them to propagate and infer causality. Many relationships have a defined "direction" indicating which of its end points is considered the "upstream" case frame and which the "downstream" case frame. The use of functionally generated case frames for the processes of increase and decrease also facilitate a simple and elegant implementation of a powerful feature: an increase or decrease can itself direct an increase or decrease. For example, to express "X suppresses the increase of Y by Z", we simply state "X-|(Z^Y)", where the inner function specifies the increase of Y by Z and the outer function operates on X and the case frame for Z^Y.

Figure 2:
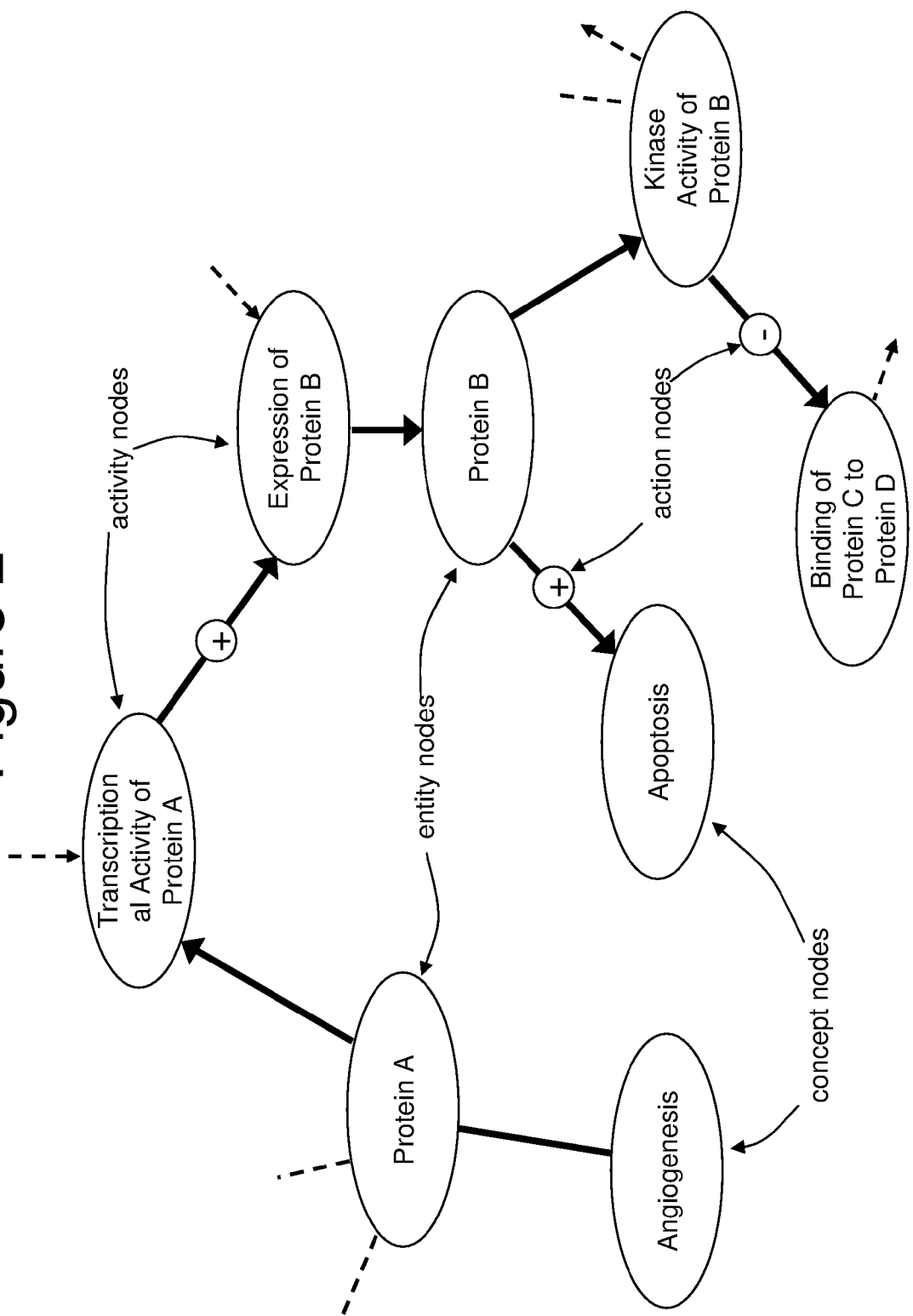
FIG. 2 is a block diagram illustrating a sequence of steps for producing models used in one embodiment of the invention.

FIG. 2 is a graphic illustration of the elemental structure of the preferred knowledge base. Thus, plural nodes, typically generated and maintained as case frames, and here illustrated as spheroids, variously represent biological entities, such as Protein A and Protein B, biological concepts, such as apoptosis or angiogenesis, activities, such as the transcriptional activity of Protein A or expression of protein B, and actions, such as +, meaning up regulate or enhance, and −, meaning down regulate or inhibit. Each nodes is connected to at least one other node, and typically to many other nodes (illustrated as dashed lines), so as to model the various biological interrelationships among biological elements and to break down the complexity of any given biological system into elemental structures and interactions. The connections in this illustration represent that there is some relationship between the nodes linked to each other. For example, Protein A is correlated with angiogenesis, but the model is silent as to whether it is a cause of angiogenesis, a result of it, or neither. Arrows here reflect the indicia in the knowledgebase of directionality of the relationship. For example, the level of Protein B is causal of the kinase activity of Protein B, but the reverse has no causal relationship; an increase in the level of Protein B also increases the biological process of apoptosis, but again, an increase in cells undergoing apoptosis in this biological system does not cause and increase in Protein B; and the kinase activity of protein B inhibits binding of Proteins C and D.

1B. Generation of Assemblies

A preferred practice of the present invention is to extract from a global knowledge base a subset of data that is necessary or helpful with respect to the specific biological topic under consideration, and to construct from the extracted data a more specialized sub-knowledge base designed specifically for the purpose at hand. In this respect, it is important that the structure of the global knowledge base be designed such that one can extract a sub-knowledge base that preserves relevant relationships between information in the sub-knowledge base. This assembly production process permits selection and rational organization of seemingly diverse data into a coherent model of any selected biological system, as defined by any desired combination of criteria. Assemblies are microcosms of the global knowledge base, can be more detailed and comprehensive than the global knowledge base in the area they address, and can be mined more easily and with greater productivity and efficiency. Assemblies can be merged with one another, used to augment one another, or can be added back to the global knowledge base.

Construction of an assembly begins when an individual specifies, via input to an interface device, biological criteria designed to retrieve from the knowledge repository all assertions considered potentially relevant to the issue being addressed. Exemplary classes of criteria applied to the repository to create the raw assembly include, but are not limited to, attributions, specific networks (e.g., transcriptional control, metabolic), and biological contexts (e.g., species, tissue, developmental stage). Additional exemplary classes of criteria include, but are not limited to, assertions based on a relationship descriptor, assertions based on text regular expression matching, assertions calculated based on forward chaining algorithms, assertions calculated based on homology, and any combinations of these criteria. Key words or word roots are often used, but other criteria also are valuable. For example, one can select assertions based on various structure-related algorithms, such as by using forward or reverse chaining algorithms (e.g., extract all assertions linked three or fewer steps downstream from all serine kinases in mast cells). Various logic operations can be applied to any of the selection criteria, such as "or," "and," and "not," in order to specify more complex selections. The diversity of sets of criteria that can be devised, and the depth of the assertions in the global knowledge base, contribute to the flexibility of use of the invention.

Assemblies created in this way usually are better than the global knowledge base or repository they were derived from in that they typically are more predictive and descriptive of real biology. This achievement rests on the application of logic during or after compilation of the raw data set so as to augment the initially retrieved data, and to improve and rationalize the resulting structure. This can be done automatically during construction of the assembly, for example, by programs embedded in computer software, or by using software tools selected and controlled by the individual conducting the exercise.

The production of an assembly thus involves a subsetting or segmentation process applied to a global repository, followed by data transformations or manipulations to improve, refine and/or augment the first generated assembly so as to perfect it and adapt it for analysis. This is accomplished by implementing a process such as applying logic to the resulting knowledgebase to harmonize it with real biology. An assembly may be augmented by insertion of new nodes and relationship descriptors derived from the knowledge base and based on logical assumptions. An assembly may be filtered by excluding subsets of data based on other biological criteria. The granularity of the system may be increased or decreased as suits the analysis at hand (which is critical to the ability to make valid extrapolations between species or generalizations within a species as data sets differ in their granularity). An assembly may be made more compact and relevant by summarizing detailed knowledge into more conclusory assertions better suited for examination by data analysis algorithms, or better suited for use with generic analysis tools, such as cluster analysis tools. Assemblies may be used to model any biological system, no matter how defined, at any level of detail, limited only by the state of knowledge in the particular area of interest, access to data, and (for new data) the time it takes to curate and import it.

In one example of assembly production, new, application oriented knowledge may be added to a global repository in a stepped, application-focused process. First, general knowledge on the topic not already in the global repository (e.g., additional knowledge regarding cancer) is added to the global repository. Second, base knowledge is gathered in the field of inquiry for the intended application (e.g., prostate cancer) from the literature, including, but not limited to, text books, scientific papers, and review articles. Third, the particular focus of the project (e.g., androgen independence in prostate cancer) is used to select still more specific sources of information. This is followed by inspection of the experimental data under consideration using the data to guide the next step of curation and knowledge gathering. For example, experimental data may show which genes and proteins are involved in the area of focus.

Figure 3:
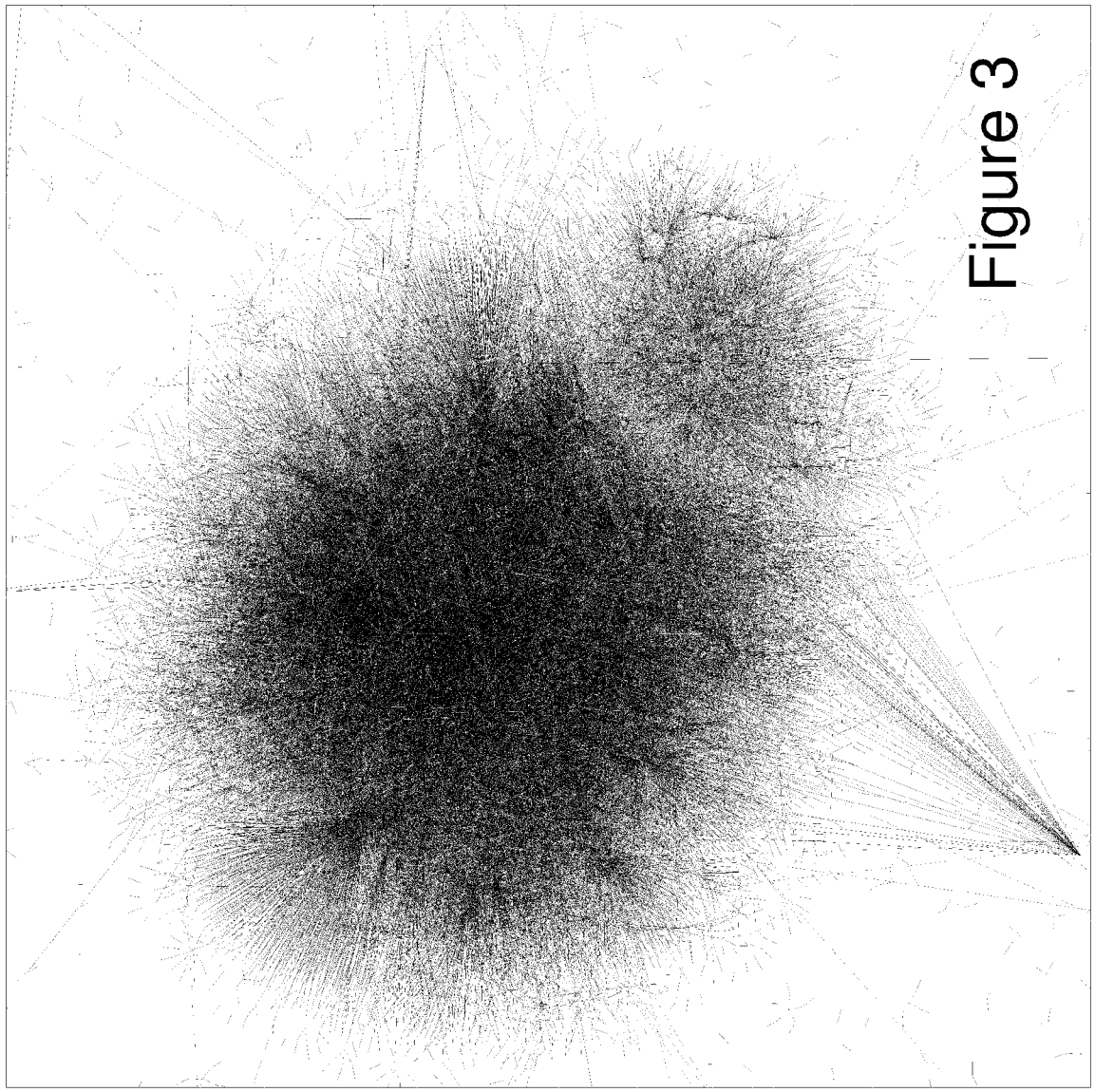
FIG. 3 is a graphical representation of a biochemical network embodied within a data base comprising an assembly directed toward a selected biological system (here generalized human biology). As is apparent the complexity of the system is far beyond human cognitive comprehension, and such graphical representations have limited utility.

FIG. 3 is a graphical representation of an assembly embodying approximately 427,000 assertions, some 204,000 nodes, and their connections. A knowledge base from which this assembly was derived is much larger and much more complex. As shown, the assembly itself can be very large, and when graphically represented takes the form of an interconnected web representative of biological mechanisms far too complex to be understood, rationalized, or used as a learning tool without the aid of computational tools. It is a collection of specific nodes and their connections within the assembly that explain a particular data set that represents the raw work product resulting from the practice of the invention, and forms the basis of a causal analysis.

1C. Generation of Hypotheses by Simulation

Next, path finding and simulation tools are used to probe the assembly with a view to defining a set of branching paths present in the assembly. Suitable tools are described in the aforementioned U.S. application Ser. No. 10/992,973, filed Nov. 19, 2004 (U.S. publication Serial Number 20050165594). Generally, the software implemented tools permit logical simulations: a class of operations conducted on a knowledge base or assembly wherein observed or hypothetical changes are applied to one or more nodes in the knowledge base and the implications of those changes are propagated through the network based on the causal relationships expressed as assertions in the knowledge base.

These methods are use to hypothesize biological relationships, i.e., a branching paths through connected nodes in a knowledge base or assembly of the type described above, by reasoning about the downstream or upstream effects of a perturbation based on the biological knowledge represented in the system. A root node is selected in the knowledgebase. Root nodes may be selected at random, or may be known, e.g., from experiment based operational data, to correspond to a biological element which increases in number or concentration, decreases in number or concentration, appears within, or disappears from a real biological system when it is perturbed. From this node software traces via simulation preferably forward, less preferably backward, or both, within the knowledgebase from the root node through the relationship descriptors preferably downstream along a path defined by linked, potentially causative nodes to discern paths hypothetically consequence of (for downstream simulation) or responsible for (for upstream simulation) the experimentally observed or assumed perturbations in the root nodes. In one embodiment, downstream simulation is conducted from all nodes in the assembly. Many of these branching paths may involve no nodes corresponding to the operational data; others will involve a few or many nodes corresponding to the operational data.

Figure 4:
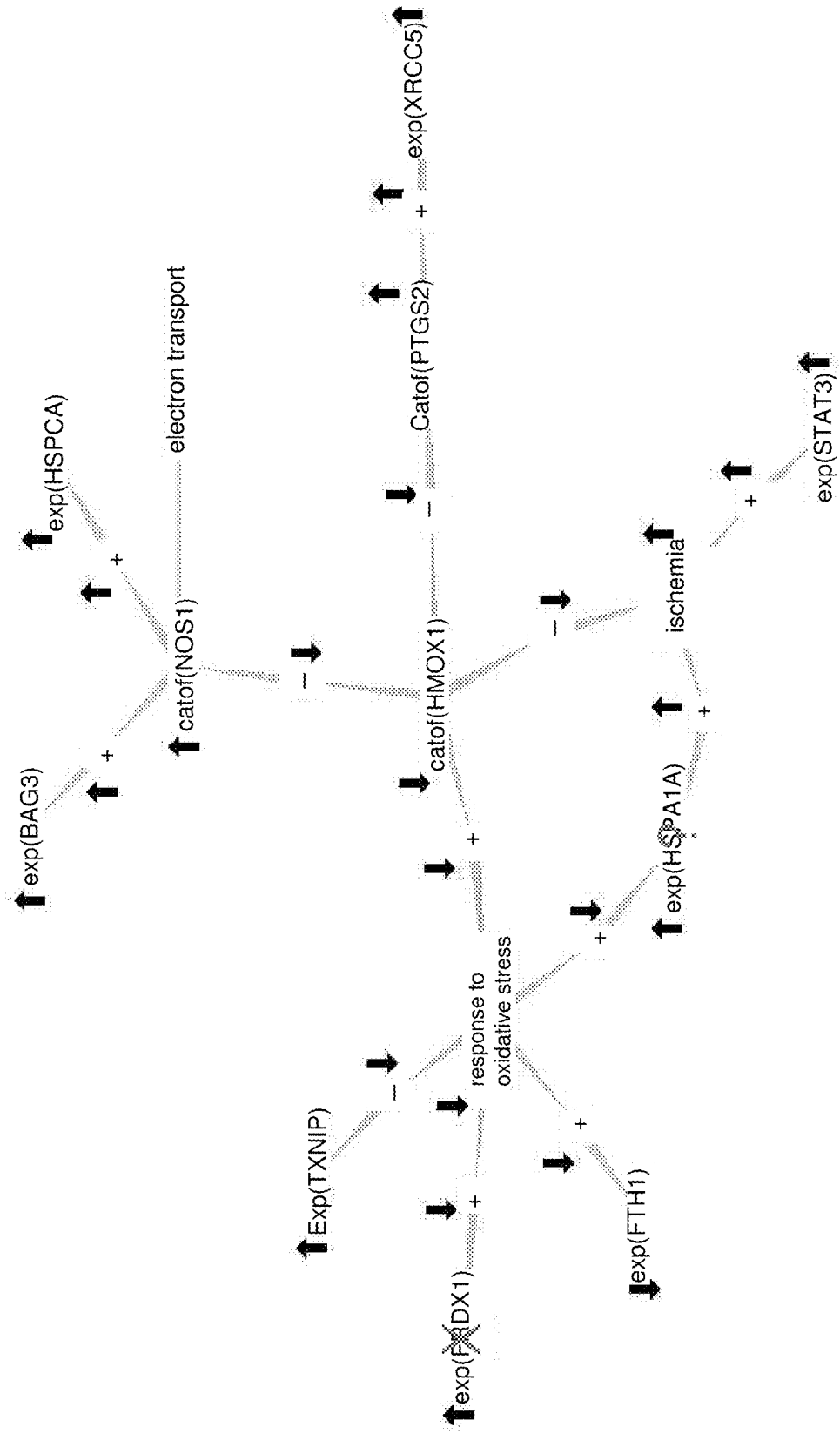
FIG. 4 is a graphical representation of a simplified "hypothesis" (branching path or model) useful in explaining the nature of the hypotheses that are pruned to deduce a causal relationship explanatory of real biology.
Figure 5:
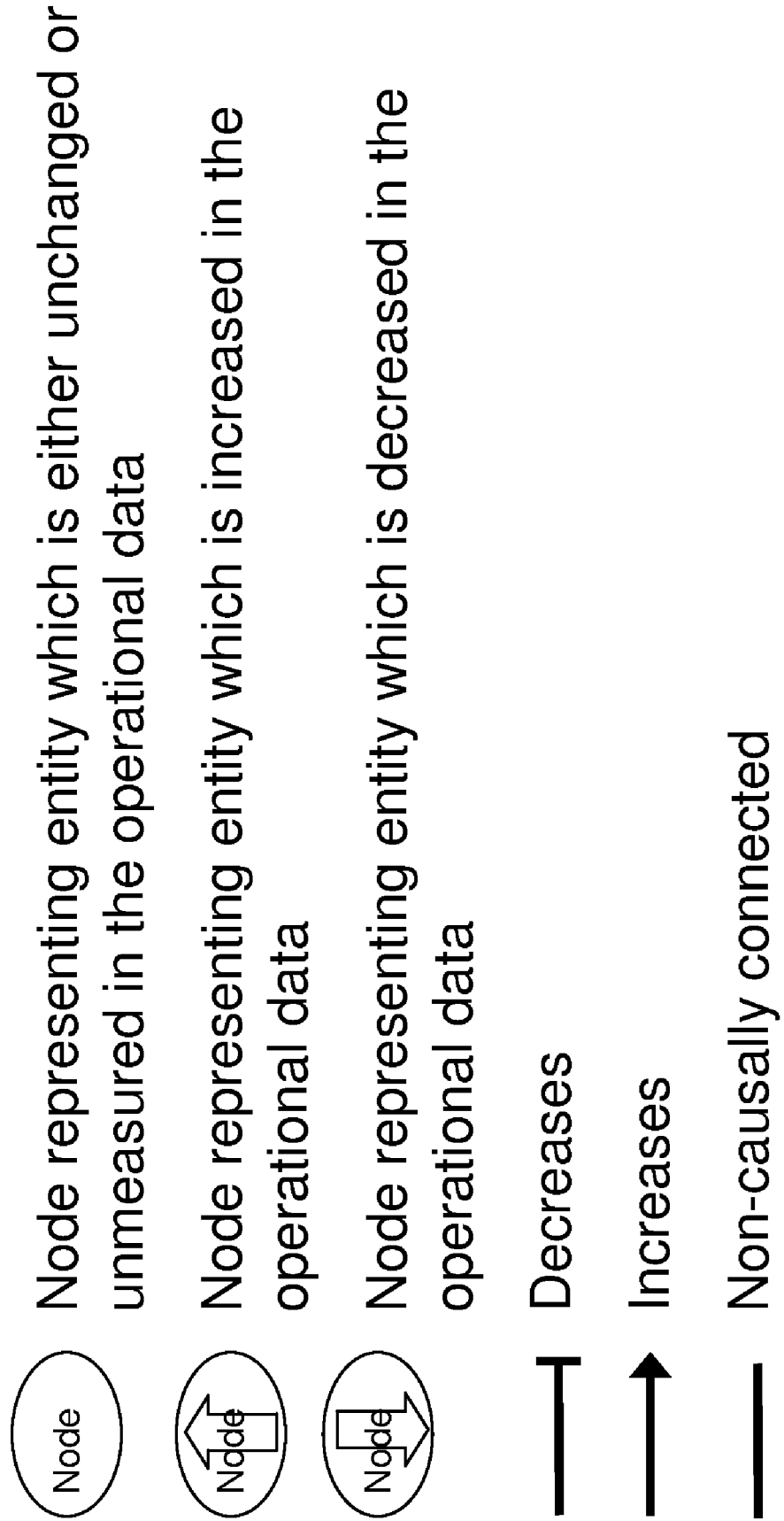
FIG. 5 is a key indicating the meaning of the various symbols used in the schematic graphical representation of a branching path illustrated in FIGS. 6 through 14.

The path finding may involve reverse causal or backward simulation, but forward simulation is preferred. Models of the chains of reasoning may be simplified by removing superfluous links. Thus, when a branching path is delineated, links or nodes which are dangling or represent dead ends in the tree, or lead to other nodes, none of which are involved in the operational data, may be removed. Typically, all nodes which have no downstream links and are not a target node are removed. This step may produce more dangling nodes, so it may be repeated until no dangling nodes are found. This action serves to identify the chains of causation in an assembly which are upstream or downstream from any selected root node and which are in some way consistent or involved with a particular set or sets of experimental measurements FIG. 4 is a simplified graphical representation of one exemplary branching path underlying a hypothesis. In this drawing, nodes are graphically represented as grey-tone vertices marked with an identification of a biological entity, action, such as increase (+) or decrease (−), functional activity, such as exp(TXNIP), or concept, such as "ischemia," or "response to oxidative stress". The node exp(TXNIP) represents the process of expression of the gene TXNIP. The root node of the hypothesis model is catof(HMOX1), representing increased catalytic activity of HMOX proteins.

Nodes which are related non-causally are connected by lines (see, e.g., catof(NOS1)-electron transport), causal connections by a triangle; the point of the triangle representing the downstream direction. For example, the model states that catof(NOS1) causes an increase (+) of exp(BAG3) and exp (HSPCA). The question mark indicates an ambiguity (the model indicates exp(HSPA1A) both increases and decreases). The exp( ) nodes correspond to operational nodes. The direction of the operational data is mapped onto the model here in the form of bolded up or down facing arrows by the exp( ) nodes. Bolded up or down facing arrows on non-operational data correspond to predictions based on the root hypothesis of increased catalytic activity of HMOX proteins, represented by the node catof(HMOX). While this model and operational data agree well, X marks a node where the model and the operational data contradict.

The operational data is the focus of the inquiry. It typically is generated from laboratory experiments, but may also be hypothetical data. The operational data set may, for example, be embodied as a spreadsheet or other compilation of increases and decreases in a set of biomolecules. For example, the data may be changes in concentrations or the appearance or disappearance of biomolecules in liver cells induced in an experimental animal such as mice or in vitro upon administration or exposure to a drug. The drug may have caused liver toxicity in one strain of mice and not in others. The question may be: what is the mechanism of the toxicity? As another example, the data may be obtained from tumor and normal tissues. In this case the question may be "what critical mechanisms are present in the tumor samples and not in the normal samples?" or "what are possible interventions that might inhibit tumor growth?" The data also may be from animals treated with different doses of a candidate drug compound ranging from non-toxic to toxic doses. It often is of interest to completely understand the mechanism of toxicity and to determine rational biomarkers diagnostic of early toxicity that emerge from this understanding. Such biomarkers may be developed as human biomarkers and used in monitoring clinical trials.

Either before or after the raw path finding step, operation data is mapped onto the nodes in the assembly, or onto the nodes in respective raw branching paths. Mapping is conducted by fitting the operational data within the network by identifying nodes that correspond to the operational data points and assigning a value (increase or decrease) correlated with the data for each node. The raw branching paths then are ranked, preferably first on the basis of the number of nodes in a candidate path that touch the operational data, and then with more sophisticated techniques. Stated differently, filtering criteria are applied to the set of branching paths based on assessments of how well a path predicts the operational data. Paths which are unlikely to represent real biology are removed from consideration as a viable hypothesis. By a process of winnowing or pruning, the methods identify one or more remaining paths comprising a theoretical basis of a new hypotheses potentially explanatory of the biological mechanism implied by the data.

By way of further explanation, in one case, a researcher may be interested in elucidating the mechanisms of some outcome in a biological system, and may conduct a series of experiments involving perturbations to the system to see which perturbations result in that outcome. An example may be a high-throughput screening experiment, such as a screen of drugs vs. one or more cell lines to see which ones produce phenotypes such as apoptosis, cell proliferation, differentiation, or cell migration. In the other case, researchers interested in a particular perturbation may take many measurements to observe effects of that perturbation. For example, the focus may be an effort in gene expression profiling involving an experiment in which a specific perturbation—drug target, over-expression, knockdown—is performed.

Mapping data from these experiments to a knowledge model, one obtains a model which, for a given depth of search, is the sum of all upstream causal hypotheses explaining the outcome. This is the "backward simulation" from the node representing the outcome. Alternatively, a model can be produced which, for a given depth of search, is the sum of all downstream causal hypotheses which predict the effects of the perturbation. This is the "forward simulation" from the node representing the quantity which is perturbed. Typically, for a given experiment and its resulting data, the first question is: "what happened in this experiment?" The answer provided by the methods disclosed herein is, first: "Here are the chains of reasoning which are present in the knowledge base and which potentially can explain the data," and second, as explained more fully below: "here are the chains that are most consistent with the observations." It is the latter models which comprise the product of the causal analysis methods disclosed herein.

1D. Hypothesis Pruning Techniques

The invention provides a class of algorithms designed to prune branching paths or models of causal explanation based on real experimental or hypothetical measurements comprising the operational data. This is done for the purpose of producing a reduced model and/or a reduced number of models representing only the causal hypotheses which are fully or partially consistent with the data and preferably with themselves. Obtaining these answers is therefore a matter of pruning the models or reducing their number by eliminating chains of reasoning inconsistent with the data and to produce a succinct, parsimonious answer or set of answers representing new hypotheses. Thus, paths which are superfluous may be pruned from within a branching path or model. This is typically a case where a short path may be eliminated in favor of a longer path that expresses greater causal detail. The criteria for "consistency with the observations" and "superfluous paths" are not absolute. The researcher can devise different definitions for these concepts and the pruned models which express the "answers" will be different.

Figure 6:
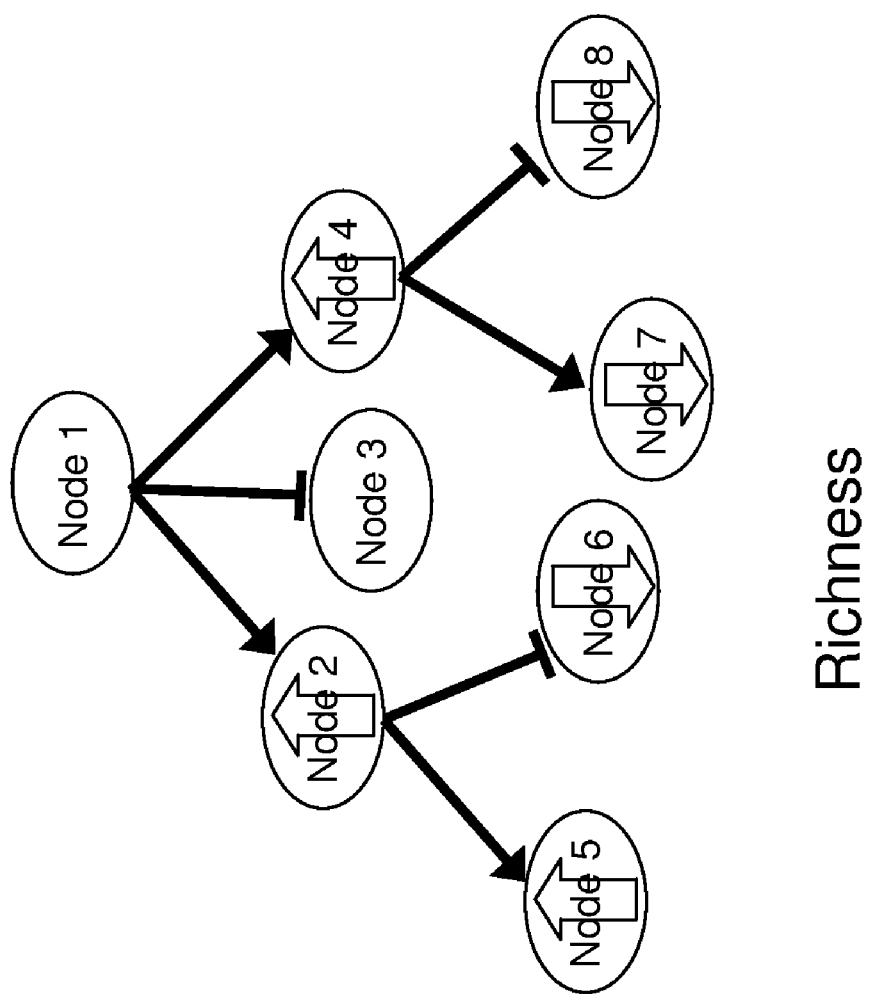
Figure 7:
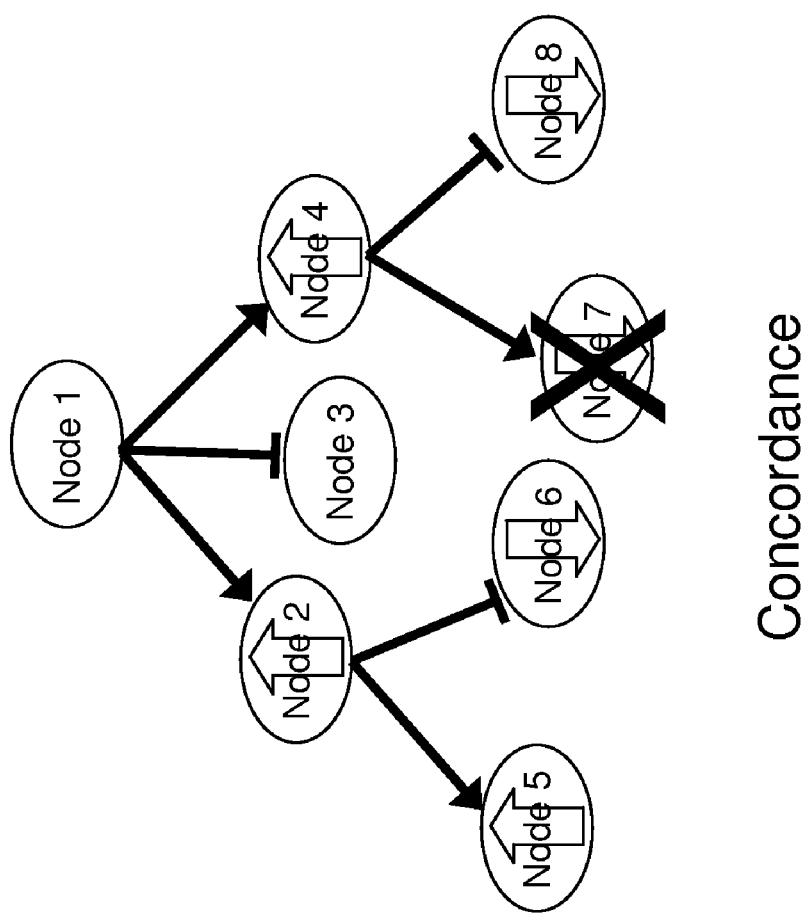

The many raw hypotheses generated by the method as set forth above preferably are reduced first by assessment of each for "richness" and "concordance." These concepts are explained with reference to FIGS. 6 and 7. As illustrated in FIG. 6, the root node is causally connected to nodes 2, 3, and 4. Node 3 has no counterpart in the operational data. Nodes 2 and 4 each are causally linked to two nodes. Of the seven nodes linked to the root node, operational data is mapped onto six. This is a "rich" hypothesis and would have a high priority. Models are favored when more than one of the plural other nodes turn out to be nodes represented by data points in the operational data. Preferably, the algorithm assesses whether the fraction of the plural other nodes linked directly to a node which map to the data is greater than the data base average fraction of plural other nodes which map to the data.

However, note that according to the model of FIG. 6, increase of node 4 should induce an increase in node 7, but the operational data shows that the entity node 7 represents in fact is decreased. This leads to the concept of concordance, (see FIG. 7) which refers to resolution of the question, with respect to each model, "what fraction of nodes correspond to the operational data," i.e., what fraction of predicted increases or decreases corresponds to increases or decreases in the operational data. Models with high concordance are preferred over models with lower concordance. There is a trade-off between richness and concordance (only one of many such trade-offs encountered in the pruning of raw hypotheses) which is addressed by setting criteria which may be rather subjective and depend on the desired output of the system.

After application of richness and concordance algorithms, in a typical exercise, the number of surviving models may range from tens to thousands, depending on the criteria applied, the granularity of the assembly, the biological focus of the model, etc. Next, one or more, typically many, logic based algorithms are applied to remaining hypotheses to further prune the models and to approach a mechanism reflective of real biology. Several currently preferred pruning and prioritization techniques are discussed below. Others can be devised by persons of skill in the art.

Figure 8:
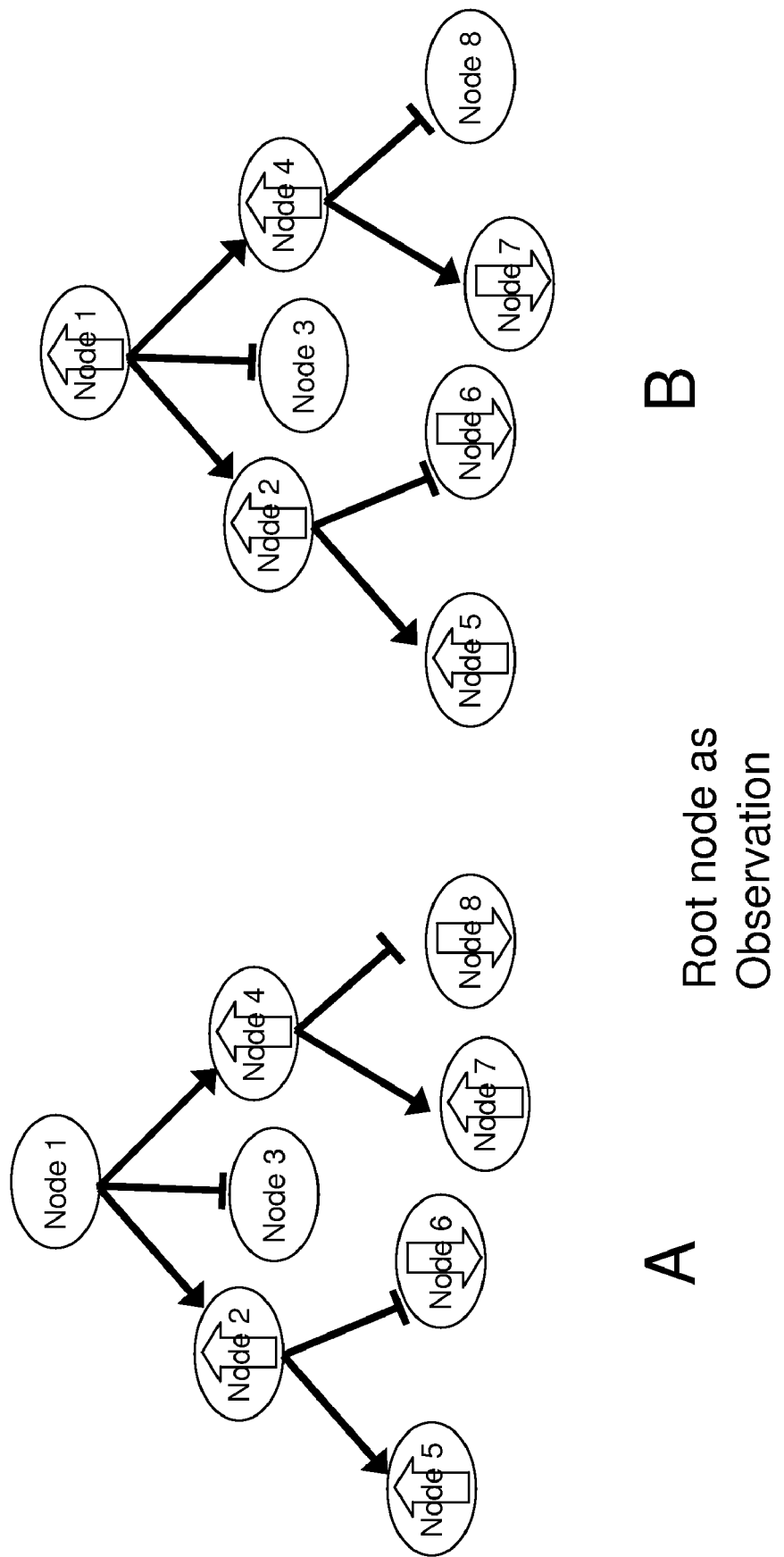

Perhaps the simplest logic based criteria, after richness and concordance, is to search for models where the root node represents an entity that appears and is in accordance with the operational data. For example, as shown in FIG. 8, models A and B have the same root, define the same pathways, and have the same richness and concordance. However, model B is preferred as the root node corresponds (is in concordance with) the operational data. Another example appears in FIG. 9. Here, again, models A and B have the same root, define the same pathways, and have the same richness and concordance. In this case model A is preferred as plural nodes mapping to the data appear in a chain, and therefore model A has a higher probability of representing real biology than model B.

Another criterion is illustrated in FIG. 10. If model A is a previously selected hypotheses, Model C is preferred over Model B because there is less overlap between the observational data explained by model A and model C. Model C therefore is more likely to be informative and helpful in discovering new real biology in this exercise.

Figure 11:
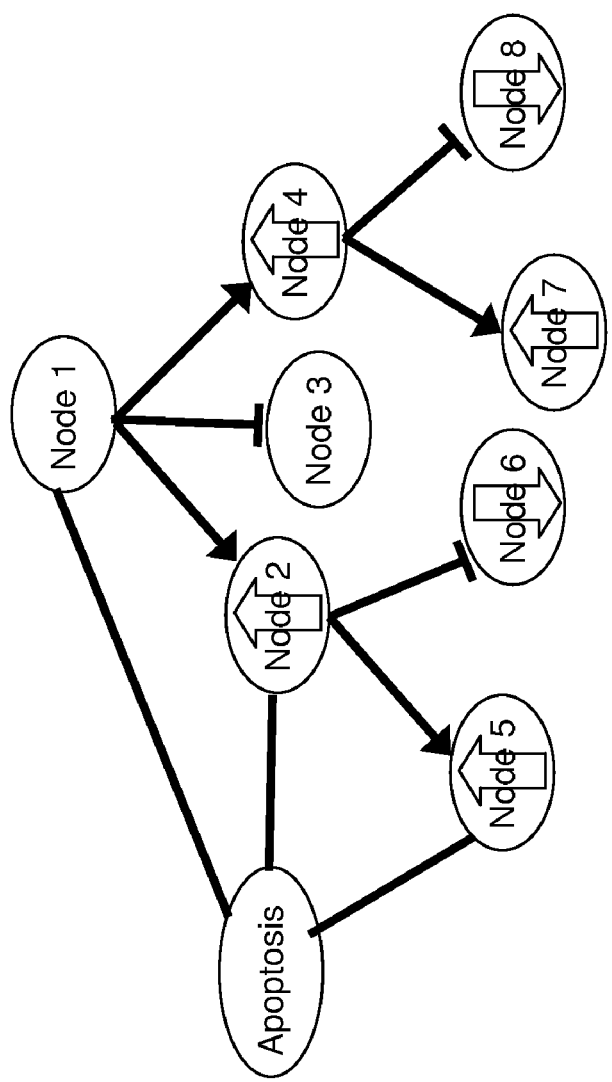

FIG. 11 illustrates one of a series of pruning criteria bases on the extent to which a given model is in accordance with known biology. This type of algorithm need not necessarily involve operational data mapping. When, as preferred, the assembly includes non causal data, these often can be used to eliminate models as not possibly representative of real biology, or to raise a score of the model because it fits well with known biology.

As illustrated in the model of FIG. 11, three nodes, two of which map to and are concordant with the operational data, are each connected to the concept node "apoptosis." If the biology under study involves apoptosis, this model is favored over others which comprise fewer such links. Models comprising multiple non causal links that correctly map to entries in knowledge bases of proteins or genes, such as GO categories, etc. are preferred. Generally, models exhibiting multiple causal connections to a concept node or to a phenotype involved in the biology under study also are preferred.

Another particularly powerful known biology-based algorithm exploits "locality," the location implied by interactions, addressing the question: "are the entities represented by the nodes in a model known to be in anatomical proximity?" Thus, in curating the knowledge base or assembly, explicit translocation events can specify that transportation of particular entities between locations is possible. Things which bind, touch, participate in reactions, transcription factor activity, are all "direct", their participants must be in the same locality or location even if the exact location is unknown. If a direct interaction process has no designated location, or if it is only known to occur in a general location, it nonetheless may only occur if its participants are available in the same locality. If interactions which are direct—either explicitly or by class (all reactions) are identified, it is possible to attempt to find hypotheses in which each step satisfies the constraints of locality.

Thus, the locality filter removes or downgrades the priority of models where the entities are known (by virtue of non causal connections in the assembly) to reside in different organelles, different cell types, different tissues, or even different species, etc. Conversely, as illustrated in FIG. 12, models comprising multiple nodes representing functions or structures known to be present in an anatomical or microanatomical locality under study, and therefore mutually anatomically accessible, are preferred.

This figure and example also include mapped operational data and illustrate that they are consistent with the model, but this is an optional feature.

Figure 13:
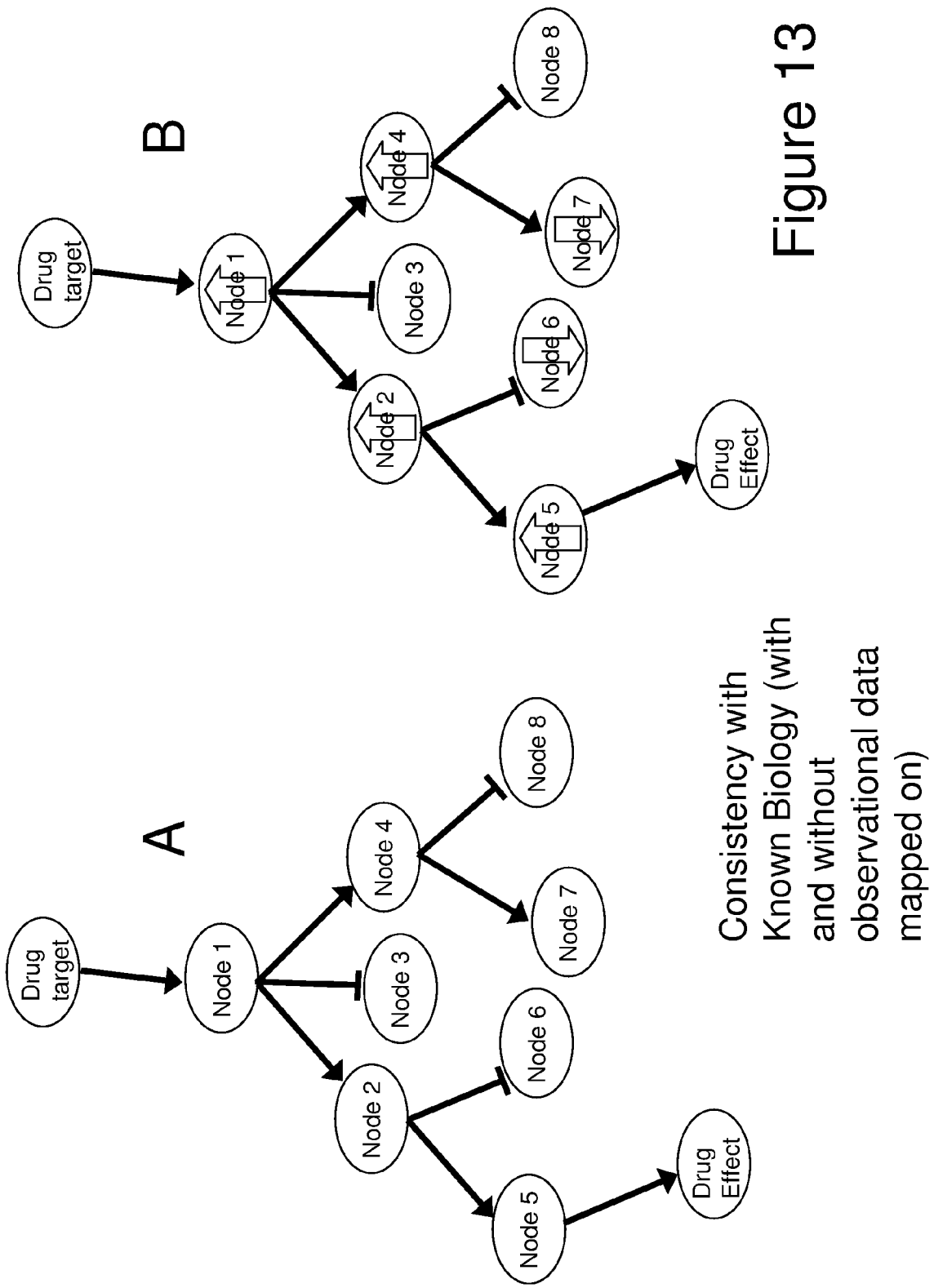

The latter point may be understood better with reference to FIG. 13. Here, two copies of the same model are shown illustrating a path from a drug target node to a drug effect concept node. In model A, none of the operational data map to the nodes, but this might still be a plausible mechanism, if, for example, no measurements were made of the activities represented by these nodes in generation of the operational data set. In model B, the path is revealed to be rich (six nodes involve operational data) and high in concordance (five of the six nodes correctly predict the direction of the data).

Yet another real biology-based criterion is illustrated in FIG. 14. Here, model B is favored over A because multiple nodes connect to the phenotype under study. Again, it is more likely that B represents real biology and will be informative of the mechanism of the biology under study.

Another type of algorithm applied to prune raw or rich hypotheses involves mapping the models against random or control data, and then using the models as a filter. In this approach, some basic statistical scores are developed for a number of hypotheses derived from a set of state changes. These same statistical scores are calculated for these hypotheses scored using random datasets generated to have similar network connectedness as the original dataset. Statistical scores based on the original data must be more significant than scores based on randomized data in order for the hypothesis to be considered further.

It is also possible to determine whether a plurality of models together best correlate with the operational data This may be done by applying a genetic or other algorithm designed to search combinatorial space to multiple models with nodes in common, with the number of correct node simulations as a fitness function.

This pruning exercise results in a smaller number of models, small enough to be examined in detail by a trained biologist, who will apply his knowledge to decide which of the hypotheses are likely to be viable explanations of the operational data. It is often possible to combine hypotheses into a more complex unified hypotheses. Even at this stage, because of the complexity of systems biology, there may be mutually exclusive hypotheses. Some may be eliminated from further consideration on various rational grounds not embodied in the assembly. Others may suggest additional experiments which can validate or refute the hypothesis.

Thus it can be appreciated that these methods and systems provide an engine of discovery of new biological causes and effects, facts, and principles, and provide a valuable analysis tool useful in advancing knowledge of the mechanisms of biological development, disease, environmental effects, drug effects, toxicities and the biological basis of diverse phenotypes, all on a detailed biochemical and molecular biology level.

The knowledgebase may be augmented perpetually as assertions from new sources are curated and incorporated in a way designed to permit many diverse analyses, and periodically or constantly updated with new knowledge reported in the academic or patent literature. As a follow-on to a causal analysis exercise, the method may further comprising the step of simulating operation of the model to make predictions about selected biological systems. Simulations may enable selection of biomarkers indicative of drug efficacy, toxicity, biological state, species (e.g., of an infectious microbe), or have other predictive value. Biomarkers may be developed which enable stratification of patients for a clinical trial, or which are of diagnostic or prognostic value. Simulations also may reveal biological entities for drug modulation of selected biological systems. The simulation also may be designed to inform selection of an animal model for drug testing that will be more informative of the drug's effects in humans.

The discovery methods may be practiced by an entity which sets up a knowledge base and writes the software needed to implement the analysis as disclosed herein. The knowledgebase, or an assembly extracted and based on a portion of it, may reside in memory on a computer any where in the world, and the various data manipulations leading to a causal analysis as disclosed herein implemented in the same or a different location, on the same or a different computer, or dispersed over a network. In one aspect, the process permits discovery by an investigator of causative relationship mechanisms in the biology of a selected biological system, and comprises causing a second party entity or entities, e.g., an outside contractor or a separate group maintained within a pharmaceutical company to do one or a combination of the steps of providing the a data base, applying an algorithm to the knowledgebase to identify plural models, mapping onto the data base the operational data, and applying to the set of models filtering criteria based on assessments of how well a model predicts the operational data as disclosed herein. The second party entity may then deliver a report to the investigator based on the analysis proposing a hypothesis or multiple hypotheses potentially explanatory of the biological mechanism implied by the data. The investigator typically will supply the operational data to a second party entity. The investigator may be situated in the country where this patent is in force and the second party entity may be outside the country where this patent is in force.

Figure 15:
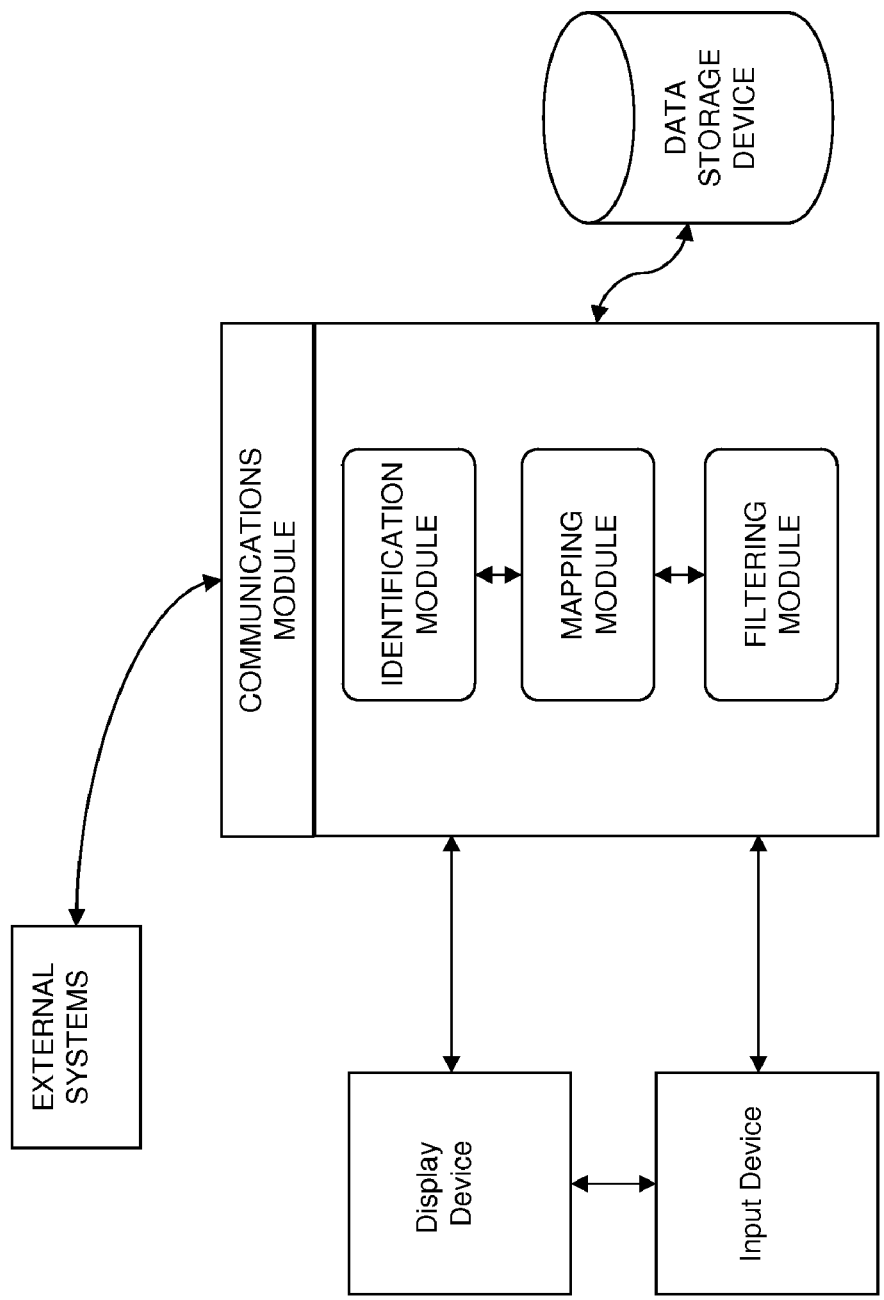
FIG. 15 is a block diagram of an apparatus for performing the methods described herein.

FIG. 15 schematically represents a hardware embodiment of the model building/hypothesis generating apparatus of the invention. As shown, it is realized as an apparatus discovering causative relationship mechanisms within a biological system using the techniques described above. The apparatus comprises a communications module, an identification module, a mapping module and a filtering module. In some embodiments, the invention also includes a knowledgebase module for storing the data described above in one or more database servers, examples of which include the MySQL Database Server by MySQL AB of Uppsala, Sweden, the PostgreSQL Database Server by the PostgreSQL Global Development Group of Berkeley, Calif., or the ORACLE Database Server offered by ORACLE Corp. of Redwood Shores, Calif.

The communication module sends and receives information (e.g., operational data as described above), instructions queries, and the like from external systems. In some embodiments, a communications network connects the apparatus with external systems. The communication may take place via any media such as standard telephone lines, LAN or WAN links (e.g., T1, T3, 56 kb, X.25), broadband connections (ISDN, Frame Relay, ATM), wireless links (802.11, bluetooth, etc.), and so on. Preferably, the network can carry TCP/IP protocol communications, and HTTP/HTTPS requests made apparatus. The type of network is not a limitation, however, and any suitable network may be used. Non-limiting examples of networks that can serve as or be part of the communications network include a wireless or wired ethernet-based intranet, a local or wide-area network (LAN or WAN), and/or the global communications network known as the Internet, which may accommodate many different communications media and protocols. Examples of exemplary communication modules include the APACHE HTTP SERVER by the Apache Software Foundation and the EXCHANGE SERVER by MICROSOFT.

The identification module identifies one or more models within the biological knowledge base (shown, for example, in FIG. 1) that are potentially relevant to the functional operation of the biological system of interest using the techniques described above. The mapping module combines the received operational data and the models identified by the identification module, which can then be filtered by the filtering module based on assessments of whether a particular model predicts the operational data. The filtering module can remove models from consideration as a viable hypotheses, and thereby permits the identification of remaining models that can be used to provide potentially explanatory hypotheses relating to the biological mechanism implied by the data. Upon identification of one or more models and/or biomarkers indicative of the biological state under study, electronic representations (e.g., data tables, graphical images, collections of nodes and/or relationships) of such models and biomarkers may be stored onto a computer-readable medium (e.g., optical or magnetic disk). These disks may then be provided to other entities for further analysis and testing.

The apparatus can also optionally include a display device and one or more input devices. Results of the mapping and filtering processes can be viewed graphically using a display device such as a computer display screen or hand-held device, but only very small portions of the model typically are comprehensible to a human through visual inspection. Where manual input and manipulation is needed, the apparatus receives instructions from a user via one or more input devices such as a keyboard, a mouse, or other pointing device.

Each of the components described above can be implemented using one or more data processing devices, which implement the functionality of the present invention as software on a general purpose computer. In addition, such a program may set aside portions of a computer's random access memory to provide control logic that affects one or more of the functions described above. In such an embodiment, the program may be written in any one of a number of high-level languages, such as FORTRAN, PASCAL, C, C++, C#, Tcl, java, or BASIC. Further, the program can be written in a script, macro, or functionality embedded in commercially available software, such as EXCEL or VISUAL BASIC. Additionally, the software may be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

2. Mapping Biomolecule Markers onto Models

Figure 16:
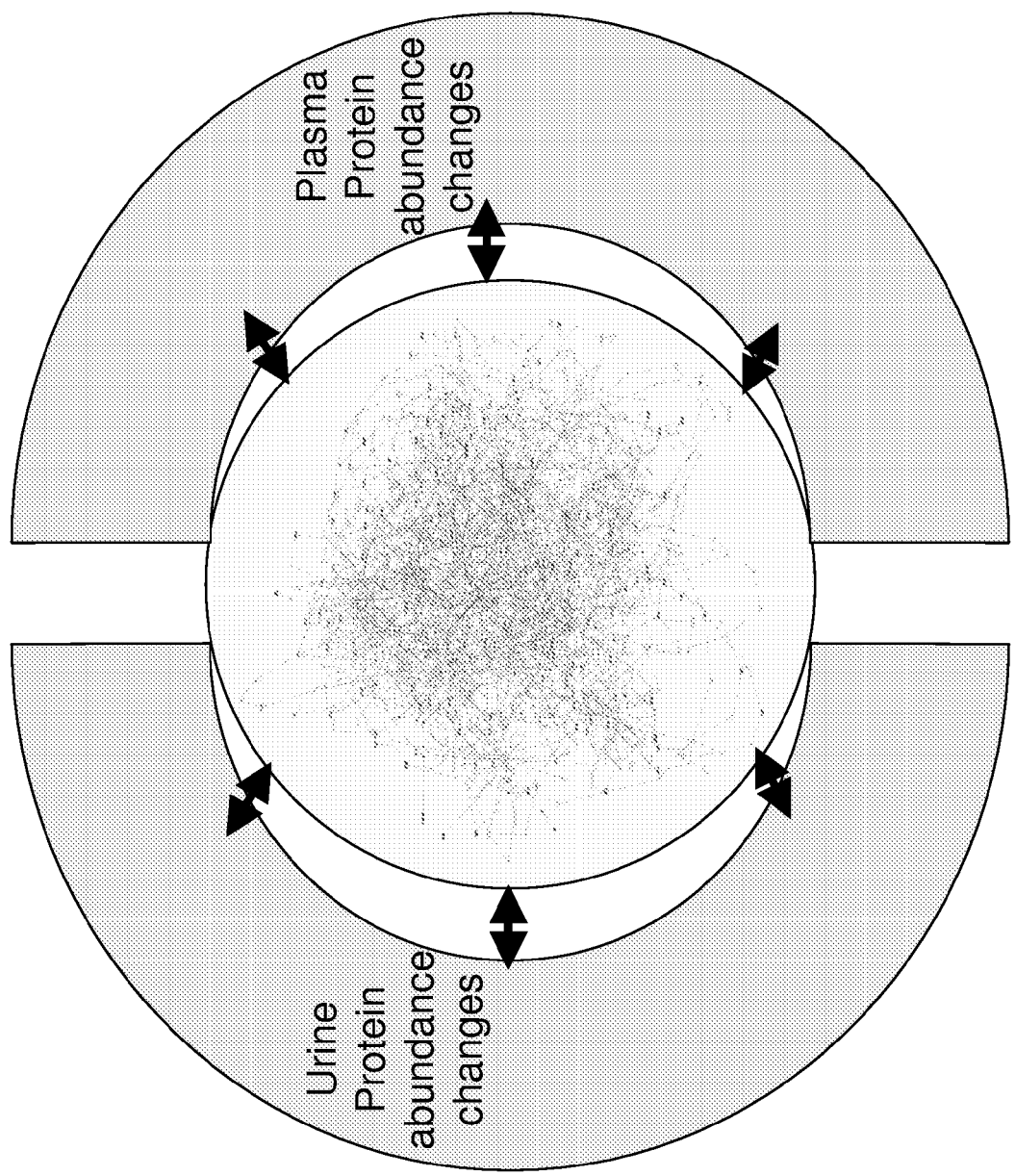
FIG. 16 is a diagram useful in illustrating a fundamental concept of the invention.

The relation between biomolecular changes observed in body fluids such as plasma or urine and in a diseased cell, tissue, organ, organism or organ system often is unclear. Fundamental to this invention is that a causal system model (CSM) of the diseased organ generated as set forth above may be used to identify key molecular networks associated with disease state, and that the model may be used to improve, validate, or help direct a search for informative biomarkers. Thus, practice of the invention may suggest addition or deletion of candidate components identified empirically in an accessible body fluid thought to be characteristic of the diseased organ, or to direct a search in a body fluid for biomarkers predicted by the model to be present in samples from diseased individuals. This mechanistic biomarker analysis is illustrated schematically in FIG. 16. A graphical illustration of a causal system model of diseased target tissue is illustrated as the central element of the process. It comprises a collection of connected nodes representing a causal biochemical/molecular biological model of a disease. Flanking the model is a urine compartment and a plasma compartment within which are measured changes in abundance of biomolecules observed in test individuals vs. controls. The methods of the invention use the model to determine which observed changes in the urine or plasma compartment are characteristic of the biological state under study and which are artifacts not directly related to the state. Informative biomolecules predicted by the CSM may be directly within the CSM (i.e., may be a protein, protein breakdown product, or metabolite, for example, that is characteristic of the biological state and should appear in the body fluid), or may not be within the CSM. In the latter case, the knowledgebase and the tools used to probe it may be used to predict which biomolecules upstream or downstream of a component within the CSM should appear in the body fluid.

Figure 17:
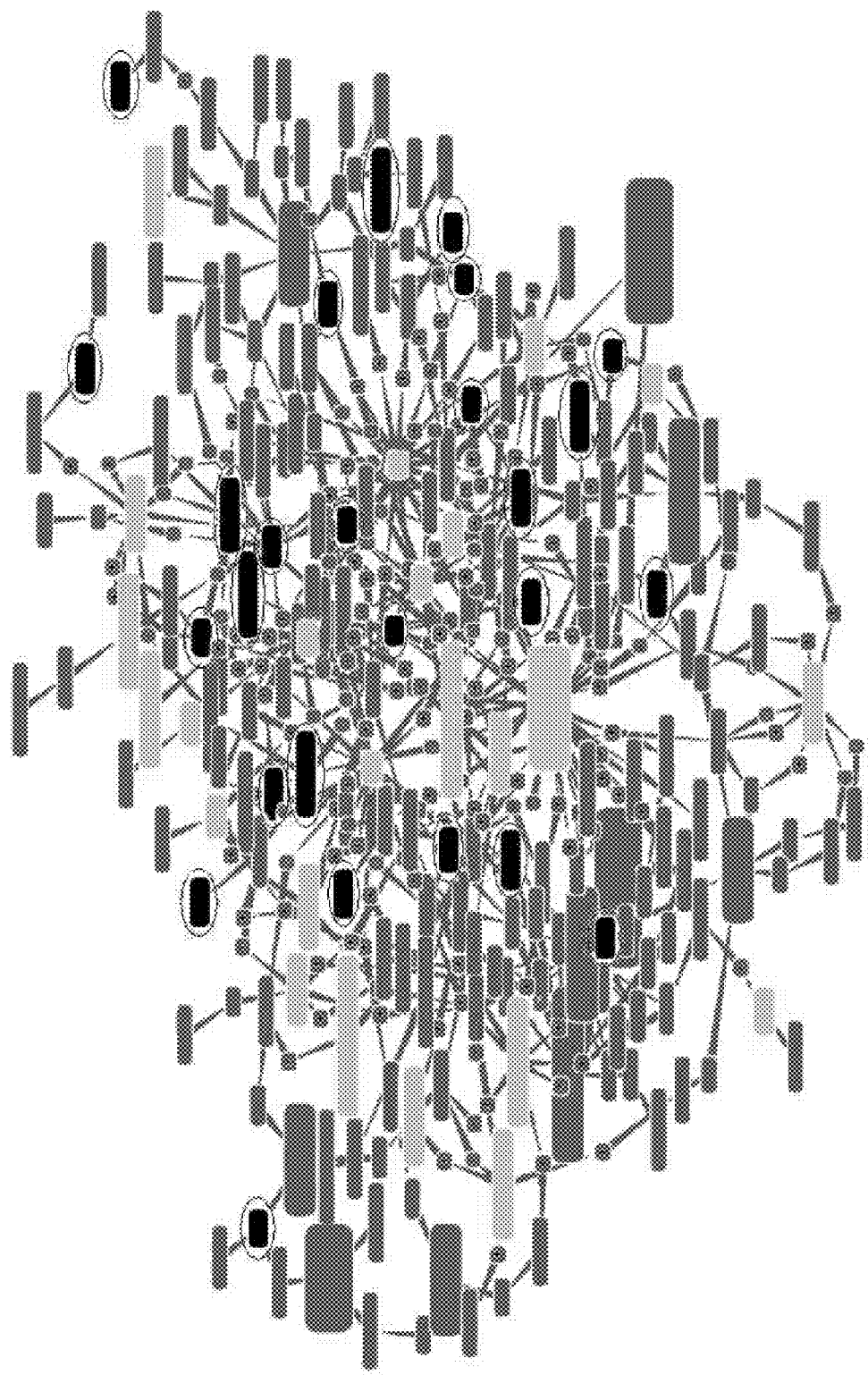
FIG. 17 is a simplified graphical representation of a causal system hypothesis, with nodes in the model represented by rectangles of various sizes, and the nodes (biomolecules) selected as components of a biomarker characteristic of the biological state shown encircled.

FIG. 17 graphically illustrates a simple CSM. The rectangular grey boxes connected to others represent nodes comprising the CSM. Circled nodes represent biomarker candidates causally connected to the model. The biomarkers are selected because the model predicts that they should appear or change in abundance and should be present in a sample from an animal in the biological state under investigation.

The invention may be practiced in at least two ways. In one approach, biomolecules and related concentrations of biomolecules that are identified empirically from samples of animals in the biological state of interest are assessed, i.e., mapped onto or compared with, a causal model such as one of the types produced above. For example, samples obtained from an association study thought to be individually or collectively indicative of the biological state can be compared with a model to identify the biomolecules (including concentrations of biomolecules and/or sets of biomolecules and biomolecule concentrations) to discern candidate biomarkers for the biological state.

In this approach, candidate biomolecules identified from the samples that do not appear to be involved in the underlying biology (as indicated by their absence from the model or models, or by their predicted absence from accessible body fluids from the mammal) may be eliminated as candidates for inclusion in a profile. Biomolecules predicted by the model, for example, to be increased in concentration, or to appear in the blood or other sample as a consequence of the biological state, and found in the empirical association study, may be included. The included biomolecules represent candidate biomarkers.

In a second approach, a causal model is created and examined to identify biomolecules (including concentrations of biomolecules and/or sets of biomolecules and biomolecule concentrations) that should be (are predicted by a model to be) present, absent, increased in abundance, or decreased in abundance, in test samples as compared with control samples.

In this second approach, before starting an empirical study, such as an association study attempting to develop a profile of some biological state of a cell or tissue, e.g., a tumor, a causal analysis may be performed to produce detailed biochemical mechanistic hypotheses underlying the biological state. The biomolecules involved in these models, or those associated with biomolecules directly involved in the model, e.g., downstream entities, then may be examined to determine which, as compared to a "normal" biochemistry of a cell, tissue, organ or organ system of an individual not in the biological state, the model predicts should be present in the sample of interest, e.g., blood. The candidate biomolecules identified by the model can be confirmed by direct empirical studies, to determine biomarkers indicative of the biological state. For example, samples from individuals known to have or be in the biological state can be used to confirm the presence of the biomolecules.

In practice, a combination of both approaches can be used to identify biomarkers, such as biomolecule profiles, or individual biomolecules and/or biomolecule concentrations. In either approach, the identity and other aspects of the candidate biomarkers can be stored in a retrievable medium for subsequent use, for example, for diagnosing and/or prognosing the biological state in an individual suspected of having the biological state.

Samples that are used to discover biomarkers and/or that are used to diagnose or prognose the biological state in an individual suspected of being in or having the biological state can be analyzed for the biomarkers using various techniques known in the art. For example, a protein biomarker can be identified or quantified using various binders, such as antibodies, cognate receptors, or aptamers. Nucleic acid biomarkers can be identified or quantified using binders such as probes complementary to a portion of the nucleic acid biomarker. The binders can be disposed on an array, for example, a microarray, to identify or quantify more than one biomarker for one or more biological states. Samples can be derived from any tissue or body fluid, for example, lymph, tears, urine, blood, serum, plasma, saliva, amniotic fluid, cerebrospinal fluid, stool, tissue lysate preparations, cell lysate preparations, or fractions thereof, that are indicative of the biological state of the cell, tissue, organ, organ system, or organism under study.

EXAMPLES

Example 1

In one application of the invention, an analysis was performed by the proprietor hereof in collaboration with a partner company. The company supplied operational data comprising 1091 changes in RNA levels observed to occur between time points in an experiment, and it was of interest to understand the biological changes occurring across the timeframe of the experiment. The knowledge base used to perform this analysis contained 1.15 million nodes and 6.28 million links. A knowledge assembly focused on human biology and proteins known to occur in the tissue of interest was constructed from the knowledge base as set forth above and in more detail in copending U.S. application Ser. No. 10/794,407 (U.S. publication Serial Number US2005-0154535A1), discussed above. Assertions based on human research present in the knowledge base were included as well as facts based on mouse or rat experiments when a homologous relationship was observed between the model organism proteins upon which the assertion was based and two human proteins found in the tissue of interest. This tissue and organism-specific assembly contained 108,344 nodes and 241,362 connections based in part on 15,292 literature citations. Hypothesis generation evaluated more than 2,166,880 potential hypotheses (models) and pruned them initially based on concordance and richness criteria. Restricting the pool of hypotheses to those statistically significant hypotheses receiving richness and concordance P values less than 0.05 yielded 1011 starting hypotheses. Comparisons to random data reduced this to 528 hypotheses. Applications of biological consistency and of other logic based criteria yielded 10 final hypotheses. Key criteria used were hypotheses that were also observed changes (6 of the final 10) and restricting to hypotheses that were causally downstream of the biological perturbation induced during the experiment. A set of 5-6 key biological concepts were used to restrict to hypotheses that were upstream of the observed and expected biological changes in the experiment. These final hypotheses, 6 of which were explicitly observed, were all downstream of the induced perturbation and upstream of observed and expected biological processes. They were combined in a causal systems model that contained 1,476 nodes based on 985 literature citations. This causal systems model can be used to find biomolecules that can be assessed to validate the model.

In accordance with this invention, the biomarker candidates identified as set forth above may be compared to biomolecules found empirically in samples from one or more individuals known to be in or suspected of being in the biological state by conducting an association study in a convenient sample, e.g., blood, urine, stool, saliva, etc. This permits assessment of the biomolecules to determine, at least as a hypothesis, which of them are associated with the biological state under study and likely to be shed into or secreted into the sample. This assessment then is available to guide validation studies.

Example 2

In another example, biomarkers were desired for a cellular process occurring in the pancreas. Pancreatic cell samples from normal and diseased rats were assayed by microarray analysis to determine 294 changed gene expressions. An assembly containing 197,788 causal relationships from 28,568 references was built. Logical simulation generated 253 hypotheses that provided explanations for the 294 state changes. Logic-based criteria were applied to prune this set of hypotheses to 17 of the most plausible. These 17 hypotheses were harmonized into a CSM that contained 795 nodes from 219 references and explained 147 of the observed changes in gene expression. Portions of the CSM contained information around nonspecific disease affects such as inflammation, while other portions of the CSM were related to biological changes specific to the disease process. This information may then be used to predict which biomolecules present in rat blood were informative of the pancreatic condition.

In another experiment involving an empirical search for biomolecules present in mouse plasma that differed as between control and test animals, 31 proteins were observed to change in the plasma between normal and diseased mice. These 31 proteins were evaluated in the context of the CSM using mouse/rat homologies and 13 were found to be mechanistically tied to the disease process modeled in the CSM. Of these 13, three were found to be mechanistically connected to the most disease specific portion of the CSM. These three were prioritized for follow-up validation.

From the foregoing it will be apparent that improved quality biomolecule profiles and surrogate markers can be developed using the invention, and have many specific uses. Thus, biomarkers may be developed that are predictors of toxic effects or efficacy of administration of a drug which permit a researcher or physician to know in advance whether the presenting patient will benefit from or be harmed by administration of the drug. Biomarkers may be developed as diagnostics or prognostic of disease, as a means of making treatment decisions, or as a means of segmenting patients in a clinical trial, thereby predisposing the trials by screening for subject patients that likely will benefit from the drug, and avoiding patients who are likely to have a toxic reaction. Such a drug might be approved for use only in patients meeting certain biomarker criteria. Biomarkers also may be used to direct therapeutic options for treatment of patients presenting with various specific malignancy.

One particularly useful technique involves the development of biomarkers using one species for use in another. For example, a liver fibrosis biomarker found in rat might also be useful for diagnosing or elucidating the extent of fibrosis of the liver in humans, as many biomolecules (like metabolites) are identical in the two species and many others have homologous structure and activity. Thus, after an exercise using, e.g., rat data, and involving test rats treated, for example, in ways not possible in humans, e.g., use of a toxic substance, induction of disease (or a model of the disease), using an unapproved drug candidate, etc., the biomarker components developed in the experimental animals, e.g., found in rat urine, may be tested for in urine from humans known to have fibrosis and from controls. Of course, rat and human biochemistry differs very significantly, but the use of homological reasoning (e.g., looking in human urine for the human form of a protein having homology with the rat form) can result in development of informative and improved biomarkers.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A software assisted method of discovering in a sample from an animal biomarkers indicative of a biological state of a cell, tissue, organ, organ system, or organism, the method comprising the steps of:
   a) providing in a storage medium one or more models representative of one or more causative or characteristic biophysical or biochemical relationships underlying the biological state in the cell, tissue, organ, organ system, or organism and comprising nodes representing a biological entity, action, functional activity, or concept, and links between nodes indicative of there being a relationship therebetween, at least some of which include indicia of causal directionality, wherein the one or more models are generated by the following sub-steps executed in a computing machine:
      providing a knowledgebase of biological assertions concerning a selected biological state, the knowledgebase comprising a multiplicity of nodes representative of a network of biological entities, actions, functional activities, and concepts, and links between nodes indicative of there being a relationship between the nodes, wherein at least some of the links comprise indicia of causal directionality;
      simulating in the network one or more perturbations of plural individual root nodes to initiate a cascade of virtual activity through said links between connected nodes to discern multiple branching paths within the knowledgebase;

mapping onto the knowledgebase operational data representative of a perturbation, associated with a biological state, of one or more nodes and optionally of experimentally observed or hypothesized changes in other nodes resulting from the one or more perturbations;

prioritizing said branching paths on the basis of how well they predict said operational data, thereby to define a set of models comprising said branching paths potentially explanatory of the molecular biology implied by the data;

applying logic based criteria to said set of models to reject models as not likely representative of real biology thereby to eliminate hypotheses and to identify from remaining models one or more active causative relationships;

b) providing a candidate set of data representative of biomolecules, or concentration relationships therebetween, determined by analysis of a sample from an animal in said biological state, and comprising lymph, tears, urine, blood, serum, plasma, saliva, amniotic fluid, cerebrospinal fluid, stool, tissue lysate preparations, cell lysate preparations, or fractions thereof, which are hypothesized to be indicative of the biological state of said cell, tissue, organ, organ system, or organism;

c) comparing the candidate set of data with the model to discern which of the biomolecules or concentration relationships therebetween are indicative of the biological state or which are not directly related to the biological state, thereby to discern a candidate biomarker for the biological state; and d) causing an electronic representation of the candidate biomarker to be physically stored on a computer-readable medium.

2. The method as described in claim 1 further including:
e) receiving samples from individuals known to be in the biological state and confirming the presence of the candidate biomarker for the biological state.

3. The method of claim 1 comprising the additional step of harmonizing a plurality of the remaining models to produce a larger model comprising a model of a portion of the operation of the biological system.

4. The method of claim 1 wherein the sample is from a species different from the species used to prepare the model, the methods comprising the additional step of applying interspecies homological reasoning to discern biomolecules in the sample homologous to biological entities in the model.

5. The method of claim 1 wherein the biological state is a disease state, toxic state, homeostatic state, a drugged state, or an environmentally stressed state.

6. The method of claim 1 wherein the biological state is a cancer of an organ or tissue or a metabolic disease.

7. The method of claim 1 wherein the logic based criteria includes a logic based criterion that is based on a measure of consistency between or among:
the predictions resulting from simulation along multiple nodes of a model and known biology of the selected biological system;
the operational data and the predictions resulting from simulation within a model upstream from a root node to a node corresponding to an operational data point;
the operational data and the predictions resulting from simulation within a model downstream from a root node to a node corresponding to an operational data point.

8. The method of claim 1 further comprising providing a data base by:
providing a data base of biological assertions comprising a multiplicity of nodes representative of biological elements and descriptors characterizing the elements or relationships among nodes;
extracting a subset of assertions from the knowledgebase that satisfy a set of biological criteria specified by a user to define a said selected biological system; and
compiling the extracted assertions to produce an assembly comprising a biological knowledge base of assertions potentially relevant to said selected biological system.

9. The method of claim 1 wherein the operational data comprises an effective increase or decrease in concentration or number of a biological element, stimulation or inhibition of activity of an element, alterations in the structure of an element, or the appearance or disappearance of an element.

10. The method of claim 1 wherein the operational data is experimentally determined data.

11. The method of claim 1 wherein the candidate set of data representative of biomolecules, or concentration relationships therebetween, comprise protein data, phosphorylation data, metabolite data, or polynucleotide data, including mRNA or the presence or absence of single nucleotide polymorphisms or other genetic characteristics.

12. The method of claim 1 comprising comparing candidate biomolecules identified from a body sample to biomolecules outside the model which the model predicts should appear in a body fluid.

13. A software assisted method of discovering in a sample from an animal biomarkers indicative of a biological state of a cell, tissue, organ, organ system, or organism, the method comprising:
a) providing in a storage medium one or more models representative of one or more causative or characteristic biophysical or biochemical relationships underlying the biological state in the cell, tissue, organ, organ system, or organism and comprising nodes representing a biological entity, action, functional activity, or concept, and links between nodes indicative of there being a relationship therebetween, at least some of which include indicia of causal directionality;
b) providing a candidate set of data representative of biomolecules, or concentration relationships therebetween, determined by analysis of a sample from an animal in said biological state, and comprising lymph, tears, urine, blood, serum, plasma, saliva, amniotic fluid, cerebrospinal fluid, stool, tissue lysate preparations, cell lysate preparations, or fractions thereof, which are hypothesized to be indicative of the biological state of said cell, tissue, organ, organ system, or organism;
c) comparing the candidate set of data with the model to discern which of the biomolecules or concentration relationships therebetween are indicative of the biological state or which are not directly related to the biological state, thereby to discern a candidate biomarker for the biological state;
d) causing an electronic representation of the candidate biomarker to be physically stored on a computer-readable medium; and
e) receiving a sample from a patient presenting for a health checkup or diagnosis, and assaying said the sample for the presence of the candidate biomarker to discern a biological state of the patient.

* * * * *